(12) United States Patent
Echarri et al.

(10) Patent No.: US 11,883,043 B2
(45) Date of Patent: Jan. 30, 2024

(54) CATHETER FUNNEL EXTENSION

(71) Applicant: DePuy Synthes Products, Inc., Raynham, MA (US)

(72) Inventors: Roberto Echarri, Raynham, MA (US); Dennis Fonseca, Raynham, MA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 477 days.

(21) Appl. No.: 16/836,437

(22) Filed: Mar. 31, 2020

(65) Prior Publication Data
US 2021/0298773 A1 Sep. 30, 2021

(51) Int. Cl.
| | |
|---|---|
| A61B 17/22 | (2006.01) |
| A61B 17/221 | (2006.01) |
| A61M 5/00 | (2006.01) |
| A61M 25/00 | (2006.01) |

(52) U.S. Cl.
CPC ........... *A61B 17/221* (2013.01); *A61M 5/007* (2013.01); *A61M 25/0021* (2013.01); *A61B 2017/2215* (2013.01); *A61B 2017/22042* (2013.01); *A61B 2017/22079* (2013.01); *A61B 2017/22094* (2013.01); *A61M 2025/0004* (2013.01); *A61M 2025/0042* (2013.01)

(58) Field of Classification Search
CPC ........ A61B 17/221; A61B 2017/22079; A61B 2017/22094; A61B 2017/2215; A61M 25/0021; A61M 2025/0004
See application file for complete search history.

(56) References Cited

U.S. PATENT DOCUMENTS

| | | |
|---|---|---|
| 4,243,040 A | 1/1981 | Beecher |
| 4,324,262 A | 4/1982 | Hall |
| 4,351,342 A | 9/1982 | Wiita et al. |
| 4,575,371 A | 3/1986 | Nordqvist et al. |
| 4,592,356 A | 6/1986 | Gutierrez |
| 4,719,924 A | 1/1988 | Crittenden et al. |
| 4,738,666 A | 4/1988 | Fuqua |
| (Continued) | | |

FOREIGN PATENT DOCUMENTS

| | | |
|---|---|---|
| CN | 1658920 A | 8/2005 |
| CN | 1972728 A | 5/2007 |
| (Continued) | | |

OTHER PUBLICATIONS

US 6,348,062 B1, 02/2002, Hopkins (withdrawn)
(Continued)

*Primary Examiner* — Kathleen S Holwerda
(74) *Attorney, Agent, or Firm* — TROUTMAN PEPPER HAMILTON SANDERS LLP

(57) ABSTRACT

The present disclosure includes a system for retrieving a blood clot in a blood vessel using a clot retrieval device having an expansile funnel that can engage with the blood clot. The present disclosure also includes a clot retrieval device having an expandable framework that can engage with the blood clot. The expansile funnel and expandable framework can expand from a collapsed delivery state to an expanded deployed state, increasing the cross-sectional area of the clot retrieval device engaging the blood clot. The increased cross-sectional area of the clot retrieval device can increase the suction force, providing effective removal of the clot from the patient.

11 Claims, 16 Drawing Sheets

(56) References Cited

U.S. PATENT DOCUMENTS

| | | |
|---|---|---|
| 4,767,404 A | 8/1988 | Renton |
| 4,793,348 A | 12/1988 | Palmaz |
| 4,873,978 A | 10/1989 | Ginsburg |
| 5,011,488 A | 4/1991 | Ginsburg |
| 5,092,839 A | 3/1992 | Kipperman |
| 5,102,415 A | 4/1992 | Guenther et al. |
| 5,122,136 A | 6/1992 | Guglielmi et al. |
| 5,123,840 A | 6/1992 | Nates |
| 5,171,233 A | 12/1992 | Amplatz |
| 5,234,437 A | 8/1993 | Sepetka |
| 5,256,144 A | 10/1993 | Kraus et al. |
| 5,261,916 A | 11/1993 | Engelson |
| 5,372,124 A | 12/1994 | Takayama et al. |
| 5,385,562 A | 1/1995 | Adams |
| 5,387,219 A | 2/1995 | Rappe |
| 5,387,226 A | 2/1995 | Miraki |
| 5,396,902 A | 3/1995 | Brennen et al. |
| 5,449,372 A | 9/1995 | Schmaltz |
| 5,520,651 A | 5/1996 | Sutcu |
| 5,538,512 A | 7/1996 | Zenzon et al. |
| 5,549,626 A | 8/1996 | Miller et al. |
| 5,558,652 A | 9/1996 | Henke |
| 5,601,600 A | 2/1997 | Ton |
| 5,609,627 A | 3/1997 | Goicoechea et al. |
| 5,624,461 A | 4/1997 | Mariant |
| 5,639,277 A | 6/1997 | Mariant |
| 5,645,558 A | 7/1997 | Horton |
| 5,658,296 A | 8/1997 | Bates |
| 5,662,671 A | 9/1997 | Barbut |
| 5,695,519 A | 12/1997 | Summer et al. |
| 5,709,704 A | 1/1998 | Nott et al. |
| 5,713,853 A | 2/1998 | Clark |
| 5,728,078 A | 3/1998 | Powers, Jr. |
| 5,769,871 A | 6/1998 | Mers Kelly |
| 5,779,716 A | 7/1998 | Cano |
| 5,810,874 A | 9/1998 | Lefebvre |
| 5,814,064 A | 9/1998 | Danniel et al. |
| 5,827,304 A | 10/1998 | Hart |
| 5,846,251 A | 12/1998 | Hart |
| 5,855,598 A | 1/1999 | Pinchuk |
| 5,893,869 A | 4/1999 | Barnhart et al. |
| 5,895,398 A | 4/1999 | Wensel |
| 5,897,567 A | 4/1999 | Ressemann |
| 5,904,698 A | 5/1999 | Thomas et al. |
| 5,911,725 A | 6/1999 | Boury |
| 5,935,139 A | 8/1999 | Bates |
| 5,938,645 A | 8/1999 | Gordon |
| 5,947,995 A | 9/1999 | Samuels |
| 5,968,057 A | 10/1999 | Taheri |
| 5,971,938 A | 10/1999 | Hart et al. |
| 5,997,939 A | 12/1999 | Moechnig et al. |
| 6,022,343 A | 2/2000 | Johnson et al. |
| 6,063,113 A | 5/2000 | Kavteladze |
| 6,066,149 A | 5/2000 | Samson et al. |
| 6,066,158 A | 5/2000 | Engelson |
| 6,093,196 A | 7/2000 | Okada |
| 6,093,199 A | 7/2000 | Brown et al. |
| 6,096,053 A | 8/2000 | Bates |
| 6,099,534 A | 8/2000 | Bates |
| 6,102,932 A | 8/2000 | Kurz |
| 6,106,548 A | 8/2000 | Roubin et al. |
| 6,129,739 A | 10/2000 | Khosravi |
| 6,142,957 A | 11/2000 | Diamond et al. |
| 6,146,396 A | 11/2000 | Kónya et al. |
| 6,146,404 A | 11/2000 | Kim |
| 6,165,194 A | 12/2000 | Denardo |
| 6,165,199 A | 12/2000 | Barbut |
| 6,168,604 B1 | 1/2001 | Cano |
| 6,168,622 B1 | 1/2001 | Mazzocchi |
| 6,174,318 B1 | 1/2001 | Bates et al. |
| 6,179,861 B1 | 1/2001 | Khosravi |
| 6,203,561 B1 | 3/2001 | Ramee |
| 6,214,026 B1 | 4/2001 | Epak |
| 6,221,006 B1 | 4/2001 | Dubrul |
| 6,238,412 B1 | 5/2001 | Dubrul |
| 6,245,087 B1 | 6/2001 | Addis |
| 6,251,122 B1 | 6/2001 | Tsukernik |
| 6,254,571 B1 | 7/2001 | Hart |
| 6,264,663 B1 | 7/2001 | Cano |
| 6,306,163 B1 | 10/2001 | Fitz |
| 6,309,379 B1 | 10/2001 | Willard |
| 6,312,407 B1 | 11/2001 | Zando-Azizi et al. |
| 6,312,444 B1 | 11/2001 | Barbut |
| 6,315,778 B1 | 11/2001 | Gambale et al. |
| 6,325,819 B1 | 12/2001 | Pavcnik et al. |
| 6,334,864 B1 | 1/2002 | Amplatz et al. |
| 6,336,934 B1 | 1/2002 | Gilson et al. |
| 6,348,056 B1 | 2/2002 | Bates |
| 6,350,271 B1 | 2/2002 | Kurz et al. |
| 6,361,545 B1 | 3/2002 | Macoviak |
| 6,371,963 B1 | 4/2002 | Nishtala et al. |
| 6,375,668 B1 | 4/2002 | Gifford et al. |
| 6,383,205 B1 | 5/2002 | Samson et al. |
| 6,383,206 B1 | 5/2002 | Gillick |
| 6,391,037 B1 | 5/2002 | Greenhalgh |
| 6,402,771 B1 | 6/2002 | Palmer |
| 6,409,683 B1 | 6/2002 | Fonseca et al. |
| 6,416,541 B2 | 7/2002 | Denardo |
| 6,425,909 B1 | 7/2002 | Dieck et al. |
| 6,432,122 B1 | 8/2002 | Gilson et al. |
| 6,436,112 B2 | 8/2002 | Wensel |
| 6,458,139 B1 | 10/2002 | Palmer |
| 6,346,116 B1 | 11/2002 | Brooks et al. |
| 6,485,497 B2 | 11/2002 | Wensel |
| 6,485,501 B1 | 11/2002 | Green |
| 6,485,502 B2 | 11/2002 | Don Michael |
| 6,511,492 B1 | 1/2003 | Rosenbluth |
| 6,517,551 B1 | 2/2003 | Driskill |
| 6,520,934 B1 | 2/2003 | Lee et al. |
| 6,520,951 B1 | 2/2003 | Carrillo, Jr. |
| 6,530,935 B2 | 3/2003 | Wensel |
| 6,530,939 B1 | 3/2003 | Hopkins |
| 6,540,768 B1 | 4/2003 | Diaz et al. |
| 6,544,279 B1 | 4/2003 | Hopkins |
| 6,551,341 B2 | 4/2003 | Boylan et al. |
| 6,551,342 B1 | 4/2003 | Shen et al. |
| 6,575,997 B1 | 6/2003 | Palmer et al. |
| 6,582,448 B1 | 6/2003 | Boyle |
| 6,585,756 B1 | 7/2003 | Strecker |
| 6,589,265 B1 | 7/2003 | Palmer et al. |
| 6,592,607 B1 | 7/2003 | Palmer et al. |
| 6,592,616 B1 | 7/2003 | Stack |
| 6,602,271 B2 | 8/2003 | Adams |
| 6,602,272 B2 | 8/2003 | Boylan et al. |
| 6,605,102 B1 | 8/2003 | Mazzocchi et al. |
| 6,610,077 B1 | 8/2003 | Hancock et al. |
| 6,616,679 B1 | 9/2003 | Khosravi |
| 6,632,241 B1 | 10/2003 | Hanoock et al. |
| 6,638,245 B2 | 10/2003 | Miller |
| 6,638,293 B1 | 10/2003 | Makower et al. |
| 6,641,590 B1 | 11/2003 | Palmer et al. |
| 6,652,555 B1 | 11/2003 | VanTassel et al. |
| 6,656,218 B1 | 12/2003 | Denardo et al. |
| 6,660,021 B1 | 12/2003 | Palmer et al. |
| 6,663,650 B2 | 12/2003 | Sepetka |
| 6,673,089 B1 | 1/2004 | Yassour et al. |
| 6,685,722 B1 | 2/2004 | Rosenbluth |
| 6,692,504 B2 | 2/2004 | Kurz et al. |
| 6,692,508 B2 | 2/2004 | Wensel |
| 6,692,509 B2 | 2/2004 | Wensel |
| 6,702,782 B2 | 3/2004 | Miller |
| 6,712,834 B2 | 3/2004 | Yassour et al. |
| 6,726,701 B2 | 4/2004 | Gilson et al. |
| 6,730,104 B1 | 5/2004 | Sepetka |
| 6,726,703 B2 | 8/2004 | Broome et al. |
| 6,824,545 B2 | 11/2004 | Sepetka |
| 6,855,155 B2 | 2/2005 | Denardo et al. |
| 6,878,163 B2 | 4/2005 | Denardo et al. |
| 6,890,340 B2 | 5/2005 | Duane |
| 6,913,612 B2 | 7/2005 | Palmer |
| 6,913,618 B2 | 7/2005 | Denardo et al. |
| 6,953,472 B2 | 10/2005 | Palmer et al. |
| 6,989,019 B2 | 1/2006 | Mazzocchi |
| 6,989,021 B2 | 1/2006 | Bosma et al. |

(56) References Cited

U.S. PATENT DOCUMENTS

| | | |
|---|---|---|
| 6,994,718 B2 | 2/2006 | Groothuis et al. |
| 6,997,939 B2 | 2/2006 | Linder |
| 7,004,954 B1 | 2/2006 | Voss et al. |
| 7,004,955 B2 | 2/2006 | Shen |
| 7,004,956 B2 | 2/2006 | Palmer |
| 7,008,434 B2 | 3/2006 | Kurz et al. |
| 7,033,376 B2 | 4/2006 | Tsukernik |
| 7,041,116 B2 | 5/2006 | Goto |
| 7,048,758 B2 | 5/2006 | Boyle |
| 7,058,456 B2 | 6/2006 | Pierce |
| 7,063,707 B2 | 6/2006 | Bose |
| 7,153,320 B2 | 12/2006 | Euteneuer et al. |
| 7,175,655 B1 | 2/2007 | Malaei |
| 7,179,273 B1 | 2/2007 | Palmer et al. |
| 7,220,269 B1 | 5/2007 | Ansel |
| 7,220,271 B2 | 5/2007 | Clubb |
| 7,226,464 B2 | 6/2007 | Garner et al. |
| 7,229,472 B2 | 6/2007 | DePalma et al. |
| 7,232,462 B2 | 6/2007 | Schaeffer |
| 7,288,112 B2 | 10/2007 | Denardo et al. |
| 7,306,618 B2 | 12/2007 | Demond |
| 7,316,692 B2 | 1/2008 | Huffmaster |
| 7,323,001 B2 | 1/2008 | Cubb |
| 7,331,976 B2 | 2/2008 | McGuckin, Jr. et al. |
| 7,344,550 B2 | 3/2008 | Carrison et al. |
| 7,399,308 B2 | 7/2008 | Borillo et al. |
| 7,410,491 B2 | 8/2008 | Hopkins |
| 7,452,496 B2 | 11/2008 | Brady et al. |
| 7,491,215 B2 | 2/2009 | Vale et al. |
| 7,491,216 B2 | 2/2009 | Brady |
| 7,510,565 B2 | 3/2009 | Gilson et al. |
| 7,534,252 B2 | 5/2009 | Sepetka |
| 7,556,636 B2 | 7/2009 | Mazzocchi |
| 7,582,111 B2 | 9/2009 | Krolik et al. |
| 7,594,926 B2 | 9/2009 | Inder |
| 7,604,649 B2 | 10/2009 | McGuckin et al. |
| 7,618,434 B2 | 11/2009 | Santra et al. |
| 7,662,165 B2 | 2/2010 | Gilson et al. |
| 7,670,356 B2 | 3/2010 | Mazzocchi |
| 7,691,121 B2 | 4/2010 | Rosenbluth |
| 7,691,124 B2 | 4/2010 | Balgobin |
| 7,708,770 B2 | 5/2010 | Linder |
| 7,736,385 B2 | 6/2010 | Agnew |
| 7,766,934 B2 | 8/2010 | Pal |
| 7,771,452 B2 | 8/2010 | Pal |
| 7,780,694 B2 | 8/2010 | Palmer |
| 7,780,696 B2 | 8/2010 | Daniel et al. |
| 7,819,893 B2 | 10/2010 | Brady et al. |
| 7,828,815 B2 | 11/2010 | Mazzocchi |
| 7,846,176 B2 | 11/2010 | Mazzocchi |
| 7,846,175 B2 | 12/2010 | Bonnette et al. |
| 7,850,708 B2 | 12/2010 | Pal |
| 7,887,560 B2 | 2/2011 | Kusleika |
| 7,901,426 B2 | 3/2011 | Gilson et al. |
| 7,914,549 B2 | 3/2011 | Morsi |
| 7,922,732 B2 | 4/2011 | Mazzocchi |
| 7,927,349 B2 | 4/2011 | Brady et al. |
| 7,927,784 B2 | 4/2011 | Simpson |
| 7,931,659 B2 | 4/2011 | Bose et al. |
| 7,998,165 B2 | 8/2011 | Huffmaster |
| 8,002,822 B2 | 8/2011 | Glocker et al. |
| 8,021,379 B2 | 9/2011 | Thompson et al. |
| 8,021,380 B2 | 9/2011 | Thompson et al. |
| 8,043,326 B2 | 10/2011 | Hancock et al. |
| 8,048,151 B2 | 11/2011 | O'Brien et al. |
| 8,052,640 B2 | 11/2011 | Fiorella et al. |
| 8,057,497 B1 | 11/2011 | Raju et al. |
| 8,066,757 B2 | 11/2011 | Ferrera et al. |
| 8,070,791 B2 | 12/2011 | Ferrera et al. |
| 8,088,140 B2 | 1/2012 | Ferrera et al. |
| 8,100,935 B2 | 1/2012 | Rosenbluth et al. |
| 8,109,941 B2 | 2/2012 | Richardson |
| 8,118,829 B2 | 2/2012 | Carrison et al. |
| 8,123,769 B2 | 2/2012 | Osborne |
| 8,137,377 B2 | 3/2012 | Palmer |
| 8,142,422 B2 | 3/2012 | Makower et al. |
| 8,142,442 B2 | 3/2012 | Palmer et al. |
| 8,182,508 B2 | 5/2012 | Magnuson et al. |
| 8,187,298 B2 | 5/2012 | Pal |
| 8,246,641 B2 | 8/2012 | Osborne et al. |
| 8,246,672 B2 | 8/2012 | Osborne |
| 8,252,017 B2 | 8/2012 | Paul, Jr. et al. |
| 8,252,018 B2 | 8/2012 | Valaie |
| 8,357,178 B2 | 1/2013 | Grandfield et al. |
| 8,357,179 B2 | 1/2013 | Grandfield et al. |
| 8,357,893 B2 | 1/2013 | Xu et al. |
| 8,361,095 B2 | 1/2013 | Osborne |
| 8,366,663 B2 | 2/2013 | Fiorella et al. |
| 8,372,133 B2 | 2/2013 | Douk et al. |
| 8,382,742 B2 | 2/2013 | Hermann et al. |
| 8,409,215 B2 | 4/2013 | Sepetka et al. |
| 8,419,748 B2 | 4/2013 | Valaie |
| 8,460,312 B2 | 6/2013 | Bose et al. |
| 8,460,313 B2 | 6/2013 | Huffmaster |
| 8,486,104 B2 | 7/2013 | Samson et al. |
| 8,529,596 B2 | 9/2013 | Grandfield et al. |
| 8,574,262 B2 | 11/2013 | Ferrera et al. |
| 8,579,915 B2 | 11/2013 | French et al. |
| 8,585,643 B2 | 11/2013 | Vo et al. |
| 8,585,713 B2 | 11/2013 | Ferrera et al. |
| 8,608,761 B2 | 12/2013 | Osbourne et al. |
| 8,679,142 B2 | 3/2014 | Slee et al. |
| 8,696,622 B2 | 4/2014 | Fiorella et al. |
| 8,702,652 B2 | 4/2014 | Fiorella et al. |
| 8,702,724 B2 | 4/2014 | Olsen et al. |
| 8,784,434 B2 | 7/2014 | Rosenbluth et al. |
| 8,784,441 B2 | 7/2014 | Rosenbluth et al. |
| 8,795,305 B2 | 8/2014 | Grandfield et al. |
| 8,795,317 B2 | 8/2014 | Grandfield et al. |
| 8,795,345 B2 | 8/2014 | Grandfield et al. |
| 8,814,892 B2 | 8/2014 | Galdonik et al. |
| 8,814,925 B2 | 8/2014 | Hilaire et al. |
| 8,900,265 B1 | 12/2014 | Ulm, III |
| 8,939,991 B2 | 1/2015 | Krolick et al. |
| 8,945,143 B2 | 2/2015 | Ferrera et al. |
| 8,945,172 B2 | 2/2015 | Ferrera et al. |
| 8,968,330 B2 | 3/2015 | Rosenbluth et al. |
| 9,039,749 B2 | 5/2015 | Shrivastava et al. |
| 9,072,537 B2 | 7/2015 | Grandfield et al. |
| 9,113,936 B2 | 8/2015 | Palmer et al. |
| 9,119,656 B2 | 9/2015 | Bose et al. |
| 9,138,307 B2 | 9/2015 | Valaie |
| 9,149,609 B2 | 10/2015 | Ansel et al. |
| 9,155,552 B2 | 10/2015 | Ulm, III |
| 9,161,766 B2 | 10/2015 | Slee et al. |
| 9,173,668 B2 | 11/2015 | Ulm, III |
| 9,186,487 B2 | 11/2015 | Dubrul et al. |
| 9,198,687 B2 | 12/2015 | Fulkerson et al. |
| 9,204,887 B2 | 12/2015 | Cully et al. |
| 9,221,132 B2 | 12/2015 | Bowman |
| 9,232,992 B2 | 1/2016 | Heidner |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,635 B2 | 5/2017 | Vale et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |

(56) References Cited

U.S. PATENT DOCUMENTS

| | | |
|---|---|---|
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Peterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,604 B2 | 12/2017 | Lam et al. |
| 9,833,625 B2 | 12/2017 | Waldhauser et al. |
| 10,028,759 B2 | 7/2018 | Wallace et al. |
| 10,149,692 B2 | 12/2018 | Turjman et al. |
| 10,265,086 B2 | 4/2019 | Vale |
| 10,716,915 B2 | 7/2020 | Ogle et al. |
| 10,610,668 B2 | 8/2020 | Burkholz et al. |
| 10,835,271 B2 | 11/2020 | Ma |
| 11,076,879 B2 | 8/2021 | Yee et al. |
| 2001/0001315 A1 | 5/2001 | Bates |
| 2001/0011182 A1 | 8/2001 | Dubrul et al. |
| 2001/0016755 A1 | 8/2001 | Addis |
| 2001/0041899 A1 | 11/2001 | Foster |
| 2001/0044598 A1 | 11/2001 | Parodi |
| 2001/0044634 A1 | 11/2001 | Don Michael et al. |
| 2001/0051810 A1 | 12/2001 | Dubrul |
| 2002/0002383 A1 | 1/2002 | Sepetka et al. |
| 2002/0016609 A1 | 2/2002 | Wensel |
| 2002/0022859 A1 | 2/2002 | Hogendijk |
| 2002/0026211 A1 | 2/2002 | Khosravi |
| 2002/0049468 A1 | 4/2002 | Streeter |
| 2002/0052620 A1 | 5/2002 | Barvut |
| 2002/0068954 A1 | 6/2002 | Foster |
| 2002/0072764 A1 | 6/2002 | Sepetka |
| 2002/0082558 A1 | 6/2002 | Samson |
| 2002/0091407 A1 | 7/2002 | Zadno-Azizi et al. |
| 2002/0095171 A1 | 7/2002 | Belef |
| 2002/0123765 A1 | 9/2002 | Sepetka |
| 2002/0143362 A1 | 10/2002 | Macoviak et al. |
| 2002/0156455 A1 | 10/2002 | Barbut |
| 2002/0161393 A1 | 10/2002 | Demond |
| 2002/0165576 A1 | 11/2002 | Boyle et al. |
| 2002/0173819 A1 | 11/2002 | Leeflang et al. |
| 2002/0177800 A1 | 11/2002 | Bagaoisan et al. |
| 2002/0188276 A1 | 12/2002 | Evans |
| 2003/0004536 A1 | 1/2003 | Boylan et al. |
| 2003/0004538 A1 | 1/2003 | Secrest |
| 2003/0004542 A1 | 1/2003 | Wensel |
| 2003/0009146 A1 | 1/2003 | Muni |
| 2003/0009191 A1 | 1/2003 | Wensel |
| 2003/0023204 A1 | 1/2003 | Vo et al. |
| 2003/0040769 A1 | 2/2003 | Kelley et al. |
| 2003/0040772 A1 | 2/2003 | Hyodoh et al. |
| 2003/0050663 A1 | 3/2003 | Khachin |
| 2003/0105484 A1 | 6/2003 | Boyle et al. |
| 2003/0125798 A1 | 7/2003 | Martin |
| 2003/0130682 A1 | 7/2003 | Broome et al. |
| 2003/0144687 A1 | 7/2003 | Brady et al. |
| 2003/0144689 A1 | 7/2003 | Brady et al. |
| 2003/0153940 A1 | 8/2003 | Nohilly et al. |
| 2003/0153943 A1 | 8/2003 | Michael et al. |
| 2003/0153944 A1 | 8/2003 | Phung |
| 2003/0163064 A1 | 8/2003 | Vrba |
| 2003/0163158 A1 | 8/2003 | Wlite |
| 2003/0171769 A1 | 9/2003 | Barbu |
| 2003/0176884 A1 | 9/2003 | Berrada et al. |
| 2003/0187495 A1 | 10/2003 | Cully et al. |
| 2003/0195537 A1 | 10/2003 | Dubrul |
| 2003/0195554 A1 | 10/2003 | Shen |
| 2003/0199917 A1 | 10/2003 | Knudson |
| 2003/0204202 A1 | 10/2003 | Palmer |
| 2003/0212430 A1 | 11/2003 | Bose |
| 2003/0216611 A1 | 11/2003 | Q. Vu |
| 2003/0236533 A1 | 12/2003 | Wilson |
| 2004/0010280 A1 | 1/2004 | Adams et al. |
| 2004/0010282 A1 | 1/2004 | Kusleika |
| 2004/0014002 A1 | 1/2004 | Lundgren |
| 2004/0068288 A1 | 4/2004 | Palmer et al. |
| 2004/0073243 A1 | 4/2004 | Sepetka |
| 2004/0079429 A1 | 4/2004 | Miller |
| 2004/0082962 A1 | 4/2004 | Demarais et al. |
| 2004/0093065 A1 | 5/2004 | Yachia et al. |
| 2004/0133231 A1 | 7/2004 | Maitland |
| 2004/0138692 A1 | 7/2004 | Phung |
| 2004/0153049 A1 | 8/2004 | Tewitt et al. |
| 2004/0153118 A1 | 8/2004 | Clubb |
| 2004/0193107 A1 | 9/2004 | Pierpont et al. |
| 2004/0199202 A1 | 10/2004 | Dubrul et al. |
| 2004/0260333 A1 | 12/2004 | Dubrul et al. |
| 2005/0015047 A1 | 1/2005 | Shah |
| 2005/0020974 A1 | 1/2005 | Noriega |
| 2005/0033348 A1 | 2/2005 | Sepetka |
| 2005/0038447 A1 | 2/2005 | Huffmaster |
| 2005/0038468 A1 | 2/2005 | Panetta et al. |
| 2005/0049619 A1 | 3/2005 | Sepetka |
| 2005/0049669 A1 | 3/2005 | Jones |
| 2005/0049670 A1 | 3/2005 | Jones et al. |
| 2005/0055033 A1 | 3/2005 | Eslie et al. |
| 2005/0055047 A1 | 3/2005 | Greenhalgh |
| 2005/0059993 A1 | 3/2005 | Ramzipoor et al. |
| 2005/0059995 A1 | 3/2005 | Sepetka |
| 2005/0085849 A1 | 4/2005 | Sepetka |
| 2005/0090857 A1 | 4/2005 | Kusleika et al. |
| 2005/0119524 A1 | 6/2005 | Sckine et al. |
| 2005/0119668 A1 | 6/2005 | Teague et al. |
| 2005/0125024 A1 | 6/2005 | Sepetka |
| 2005/0131449 A1 | 6/2005 | Salahieh et al. |
| 2005/0149111 A1 | 7/2005 | Kanazawa et al. |
| 2005/0171566 A1 | 8/2005 | Kanamaru |
| 2005/0187570 A1 | 8/2005 | Nguyen et al. |
| 2005/0267491 A1 | 8/2005 | Kellett et al. |
| 2005/0216030 A1 | 9/2005 | Sepetka |
| 2005/0216050 A1 | 9/2005 | Sepetka |
| 2005/0288686 A1 | 9/2005 | Sepetka |
| 2005/0228417 A1 | 10/2005 | Teitelbaum et al. |
| 2006/0009785 A1 | 1/2006 | Maitland et al. |
| 2006/0009799 A1 | 1/2006 | Kleshinski et al. |
| 2006/0010636 A1 | 1/2006 | Vacher |
| 2006/0030933 A1 | 2/2006 | DeLegge et al. |
| 2006/0036271 A1 | 2/2006 | Schomer et al. |
| 2006/0058836 A1 | 3/2006 | Bose |
| 2006/0058837 A1 | 3/2006 | Bose |
| 2006/0058838 A1 | 3/2006 | Bose |
| 2006/0064151 A1 | 3/2006 | Guterman et al. |
| 2006/0149313 A1 | 7/2006 | Arguello et al. |
| 2006/0155305 A1 | 7/2006 | Freudenthal |
| 2006/0155322 A1 | 7/2006 | Sater et al. |
| 2006/0161187 A1 | 7/2006 | Levine et al. |
| 2006/0195137 A1 | 8/2006 | Sepetka |
| 2006/0224177 A1 | 10/2006 | Finitsis |
| 2006/0224179 A1 | 10/2006 | Kucharczyk |
| 2006/0229638 A1 | 10/2006 | Abrams et al. |
| 2006/0282111 A1 | 12/2006 | Morsi |
| 2006/0287701 A1 | 12/2006 | Pal |
| 2007/0088383 A1 | 4/2007 | Pal et al. |

(56) References Cited

U.S. PATENT DOCUMENTS

| | | |
|---|---|---|
| 2007/0142858 A1 | 6/2007 | Bates |
| 2007/0149996 A1 | 6/2007 | Coughlin |
| 2007/0156170 A1 | 7/2007 | Hancock |
| 2007/0165170 A1 | 7/2007 | Fukuda |
| 2007/0179513 A1 | 8/2007 | Deutsch |
| 2007/0191866 A1 | 8/2007 | Palmer et al. |
| 2007/0198028 A1 | 8/2007 | Miloslavski |
| 2007/0198051 A1 | 8/2007 | Clubb et al. |
| 2007/0198075 A1 | 8/2007 | Levy |
| 2007/0208367 A1 | 9/2007 | Fiorella |
| 2007/0208371 A1 | 9/2007 | French |
| 2007/0213765 A1* | 9/2007 | Adams ............ A61B 17/12136 606/191 |
| 2007/0225749 A1 | 9/2007 | Martin |
| 2007/0239182 A1 | 10/2007 | Glines et al. |
| 2007/0239254 A1 | 10/2007 | Chia et al. |
| 2007/0244505 A1 | 10/2007 | Gilson et al. |
| 2007/0270902 A1 | 11/2007 | Slazas et al. |
| 2007/0288038 A1 | 12/2007 | Bimbo |
| 2007/0293887 A1 | 12/2007 | Okushi et al. |
| 2008/0045881 A1 | 2/2008 | Teitelbaum et al. |
| 2008/0082107 A1 | 4/2008 | Miller et al. |
| 2008/0086190 A1 | 4/2008 | Ta |
| 2008/0091223 A1 | 4/2008 | Pokorney |
| 2008/0097398 A1 | 4/2008 | Mitelberg |
| 2008/0109031 A1 | 5/2008 | Sepetka |
| 2008/0109032 A1 | 5/2008 | Sepetka |
| 2008/0119886 A1 | 5/2008 | Greenhalgh et al. |
| 2008/0177296 A1 | 7/2008 | Sepetka |
| 2008/0183197 A1 | 7/2008 | Sepetka |
| 2008/0183198 A1 | 7/2008 | Sepetka |
| 2008/0183205 A1 | 7/2008 | Sepetka |
| 2008/0188876 A1 | 8/2008 | Sepetka |
| 2008/0188885 A1 | 8/2008 | Sepetka |
| 2008/0188928 A1 | 8/2008 | Salahieh |
| 2008/0200946 A1 | 8/2008 | Braun |
| 2008/0215077 A1 | 9/2008 | Sepetka |
| 2008/0221600 A1 | 9/2008 | Dieck et al. |
| 2008/0228209 A1 | 9/2008 | DeMello et al. |
| 2008/0234706 A1 | 9/2008 | Sepetka |
| 2008/0243170 A1 | 10/2008 | Jenson |
| 2008/0255596 A1 | 10/2008 | Jenson |
| 2008/0262528 A1 | 10/2008 | Martin |
| 2008/0262532 A1 | 10/2008 | Martin |
| 2008/0269774 A1 | 10/2008 | Garcia et al. |
| 2008/0275488 A1 | 11/2008 | Fleming |
| 2008/0275493 A1 | 11/2008 | Farmiga |
| 2008/0281350 A1 | 11/2008 | Sepetka |
| 2008/0312681 A1 | 12/2008 | Ansel |
| 2009/0024157 A1 | 1/2009 | Anukhin |
| 2009/0054918 A1 | 2/2009 | Henson |
| 2009/0069828 A1 | 3/2009 | Martin |
| 2009/0076539 A1 | 3/2009 | Valaie |
| 2009/0105722 A1 | 4/2009 | Fulkerson |
| 2009/0105737 A1 | 4/2009 | Fulkerson |
| 2009/0131908 A1 | 5/2009 | Mckay |
| 2009/0163846 A1 | 5/2009 | Aklog et al. |
| 2009/0177206 A1 | 7/2009 | Lozier et al. |
| 2009/0182336 A1 | 7/2009 | Brenzel et al. |
| 2009/0221967 A1 | 9/2009 | Thommen et al. |
| 2009/0270815 A1 | 10/2009 | Stamp et al. |
| 2009/0281610 A1 | 11/2009 | Parker |
| 2009/0292297 A1 | 11/2009 | Ferrere |
| 2009/0292307 A1 | 11/2009 | Razack |
| 2009/0299374 A1 | 12/2009 | Tilson et al. |
| 2009/0299393 A1 | 12/2009 | Martin |
| 2009/0306702 A1 | 12/2009 | Miloslavski |
| 2010/0004607 A1 | 1/2010 | Wilson et al. |
| 2010/0016957 A1 | 1/2010 | Jager et al. |
| 2010/0030186 A1 | 2/2010 | Stivland |
| 2010/0030256 A1 | 2/2010 | Dubrul et al. |
| 2010/0036312 A1 | 2/2010 | Krolik et al. |
| 2010/0087908 A1 | 4/2010 | Hilaire |
| 2010/0114017 A1 | 5/2010 | Lenker |
| 2010/0125326 A1 | 5/2010 | Kalstad |
| 2010/0125327 A1 | 5/2010 | Agnew |
| 2010/0191272 A1 | 7/2010 | Keating |
| 2010/0211094 A1 | 8/2010 | Sargent, Jr. |
| 2010/0249815 A1 | 9/2010 | Jantzen et al. |
| 2010/0268264 A1 | 10/2010 | Bonnett et al. |
| 2010/0268265 A1* | 10/2010 | Krolik ................ A61B 17/221 606/200 |
| 2010/0292726 A1 | 11/2010 | Olsen et al. |
| 2010/0305566 A1 | 12/2010 | Rosenblatt et al. |
| 2010/0305604 A1 | 12/2010 | Pah |
| 2010/0318178 A1 | 12/2010 | Rapaport et al. |
| 2010/0324649 A1 | 12/2010 | Mattsson |
| 2010/0331949 A1 | 12/2010 | Habib |
| 2011/0009875 A1 | 1/2011 | Grandfield et al. |
| 2011/0009940 A1 | 1/2011 | Grandfield et al. |
| 2011/0009942 A1 | 1/2011 | Gregorich |
| 2011/0022149 A1 | 1/2011 | Cox et al. |
| 2011/0054514 A1 | 3/2011 | Arcand |
| 2011/0054516 A1 | 3/2011 | Keegan |
| 2011/0060359 A1 | 3/2011 | Hannes |
| 2011/0071432 A1 | 3/2011 | Carrillo, Jr. et al. |
| 2011/0077620 A1 | 3/2011 | deBeer |
| 2011/0098683 A1 | 4/2011 | Wiita et al. |
| 2011/0054504 A1 | 5/2011 | Wolf et al. |
| 2011/0125181 A1 | 5/2011 | Brady et al. |
| 2011/0130756 A1 | 6/2011 | Everson, Jr. et al. |
| 2011/0152920 A1 | 6/2011 | Eckhouse et al. |
| 2011/0160763 A1 | 6/2011 | Ferrera et al. |
| 2011/0166586 A1 | 7/2011 | Sepetka et al. |
| 2011/0196414 A1 | 8/2011 | Porter et al. |
| 2011/0202088 A1 | 8/2011 | Eckhouse et al. |
| 2011/0213290 A1 | 9/2011 | Chin et al. |
| 2011/0213297 A1 | 9/2011 | Aklog et al. |
| 2011/0213393 A1 | 9/2011 | Aklog et al. |
| 2011/0213403 A1 | 9/2011 | Aboytes |
| 2011/0218564 A1 | 9/2011 | Drasler et al. |
| 2011/0224707 A1 | 9/2011 | Miloslavaski et al. |
| 2011/0264132 A1 | 10/2011 | Strauss et al. |
| 2011/0276120 A1 | 11/2011 | Gilson et al. |
| 2011/0319917 A1 | 12/2011 | Ferrera et al. |
| 2012/0041449 A1 | 2/2012 | Eckhouse et al. |
| 2012/0041474 A1 | 2/2012 | Eckhouse et al. |
| 2012/0059356 A1 | 3/2012 | diPama et al. |
| 2012/0089216 A1 | 4/2012 | Rapaport et al. |
| 2012/0101510 A1 | 4/2012 | Lenker et al. |
| 2012/0116351 A1 | 5/2012 | Chomas et al. |
| 2012/0116440 A1 | 5/2012 | Leynov et al. |
| 2012/0143237 A1 | 6/2012 | Cam et al. |
| 2012/0143239 A1 | 6/2012 | Aklog et al. |
| 2012/0150147 A1 | 6/2012 | Leynov et al. |
| 2012/0165858 A1 | 6/2012 | Eckhouse et al. |
| 2012/0165859 A1 | 6/2012 | Eckhouse et al. |
| 2012/0215250 A1 | 8/2012 | Grandfield et al. |
| 2012/0277788 A1 | 11/2012 | Cattaneo |
| 2012/0283768 A1 | 11/2012 | Cox et al. |
| 2012/0296362 A1 | 11/2012 | Cam et al. |
| 2012/0316600 A1 | 12/2012 | Ferrera et al. |
| 2013/0006284 A1 | 1/2013 | Aggerholm et al. |
| 2013/0030461 A1 | 1/2013 | Marks et al. |
| 2013/0046330 A1 | 2/2013 | McIntosh et al. |
| 2013/0046333 A1 | 2/2013 | Jones et al. |
| 2013/0046334 A1 | 2/2013 | Jones et al. |
| 2013/0116774 A1 | 5/2013 | Strauss et al. |
| 2013/0131614 A1 | 5/2013 | Hassan et al. |
| 2013/0144326 A1 | 6/2013 | Brady et al. |
| 2013/0144328 A1 | 6/2013 | Weber et al. |
| 2013/0158592 A1 | 6/2013 | Porter |
| 2013/0184703 A1 | 7/2013 | Shireman et al. |
| 2013/0184739 A1 | 7/2013 | Brady et al. |
| 2013/0197567 A1 | 8/2013 | Brady et al. |
| 2013/0226146 A1 | 8/2013 | Tekulve |
| 2013/0268050 A1 | 10/2013 | Wilson et al. |
| 2013/0281788 A1 | 10/2013 | Garrison |
| 2013/0289697 A1 | 10/2013 | Baker et al. |
| 2013/0325055 A1 | 12/2013 | Eckhouse et al. |
| 2013/0325056 A1 | 12/2013 | Eckhouse et al. |
| 2013/0345739 A1 | 12/2013 | Brady et al. |
| 2014/0012281 A1 | 1/2014 | Wang et al. |
| 2014/0046359 A1 | 2/2014 | Bowman et al. |

(56) References Cited

U.S. PATENT DOCUMENTS

| | | |
|---|---|---|
| 2014/0052097 A1 | 2/2014 | Petersen et al. |
| 2014/0081243 A1 | 3/2014 | Zhou et al. |
| 2014/0121672 A1 | 5/2014 | Folk |
| 2014/0128905 A1 | 5/2014 | Molaei |
| 2014/0135812 A1 | 5/2014 | Divino et al. |
| 2014/0180377 A1 | 6/2014 | Bose et al. |
| 2014/0188127 A1 | 7/2014 | Dubrul et al. |
| 2014/0194919 A1 | 7/2014 | Losordo et al. |
| 2014/0200607 A1 | 7/2014 | Sepetka et al. |
| 2014/0200608 A1 | 7/2014 | Brady et al. |
| 2014/0236220 A1 | 8/2014 | Inoue |
| 2014/0257018 A1 | 9/2014 | Farnan |
| 2014/0257362 A1 | 9/2014 | Eldenschink |
| 2014/0276922 A1 | 9/2014 | McLain et al. |
| 2014/0277003 A1 | 9/2014 | Hendrick |
| 2014/0277053 A1 | 9/2014 | Wang et al. |
| 2014/0277079 A1 | 9/2014 | Vale et al. |
| 2014/0309657 A1 | 10/2014 | Ben-Ami |
| 2014/0309673 A1 | 10/2014 | Dacuycuy et al. |
| 2014/0330302 A1 | 11/2014 | Tekulve et al. |
| 2014/0343585 A1 | 11/2014 | Ferrera et al. |
| 2014/0364896 A1 | 12/2014 | Consigny |
| 2014/0371769 A1 | 12/2014 | Vale et al. |
| 2014/0371777 A1 | 12/2014 | Rudakov et al. |
| 2014/0371779 A1 | 12/2014 | Vale et al. |
| 2014/0371780 A1 | 12/2014 | Vale et al. |
| 2014/0379023 A1 | 12/2014 | Brady et al. |
| 2015/0018859 A1 | 1/2015 | Quick et al. |
| 2015/0018860 A1 | 1/2015 | Quick et al. |
| 2015/0080937 A1 | 3/2015 | Davidson |
| 2015/0081003 A1 | 3/2015 | Wainwright et al. |
| 2015/0112376 A1 | 4/2015 | Molaei et al. |
| 2015/0133990 A1 | 5/2015 | Davidson |
| 2015/0142043 A1 | 5/2015 | Furey |
| 2015/0164523 A1 | 6/2015 | Brady et al. |
| 2015/0173782 A1 | 6/2015 | Garrison et al. |
| 2015/0173783 A1 | 6/2015 | Tah et al. |
| 2015/0238314 A1 | 8/2015 | Börtlein et al. |
| 2015/0250497 A1 | 9/2015 | Marks et al. |
| 2015/0257775 A1 | 9/2015 | Gilvarry et al. |
| 2015/0258270 A1 | 9/2015 | Kunis |
| 2015/0290437 A1 | 10/2015 | Rudakov et al. |
| 2015/0297252 A1 | 10/2015 | Miloslavski et al. |
| 2015/0306311 A1 | 10/2015 | Pinchuk et al. |
| 2015/0313617 A1 | 11/2015 | Grandfield et al. |
| 2015/0320431 A1 | 11/2015 | Ulm, III |
| 2015/0351770 A1 | 12/2015 | Fulton, III |
| 2015/0352325 A1 | 12/2015 | Quick |
| 2015/0359547 A1 | 12/2015 | Vale et al. |
| 2015/0374391 A1 | 12/2015 | Quick et al. |
| 2015/0374393 A1 | 12/2015 | Brady et al. |
| 2015/0374479 A1 | 12/2015 | Vale |
| 2016/0015402 A1 | 1/2016 | Brady et al. |
| 2016/0022296 A1 | 1/2016 | Brady et al. |
| 2016/0066921 A1 | 3/2016 | Brady et al. |
| 2016/0074067 A1 | 3/2016 | Furnish et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113664 A1 | 4/2016 | Brady et al. |
| 2016/0113665 A1 | 4/2016 | Brady et al. |
| 2016/0120558 A1 | 5/2016 | Brady et al. |
| 2016/0121080 A1 | 5/2016 | Cottone |
| 2016/0135829 A1 | 5/2016 | Holochwost et al. |
| 2016/0143653 A1 | 5/2016 | Vale et al. |
| 2016/0151079 A1 | 6/2016 | Aklog et al. |
| 2016/0192953 A1 | 7/2016 | Brady et al. |
| 2016/0192954 A1 | 7/2016 | Brady et al. |
| 2016/0192955 A1 | 7/2016 | Brady et al. |
| 2016/0192956 A1 | 7/2016 | Brady et al. |
| 2016/0228134 A1 | 8/2016 | Martin et al. |
| 2016/0256180 A1 | 9/2016 | Vale et al. |
| 2016/0262880 A1 | 9/2016 | Li et al. |
| 2016/0317168 A1 | 11/2016 | Brady et al. |
| 2016/0346002 A1 | 12/2016 | Avneri et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0065401 A1 | 3/2017 | Fearnot et al. |
| 2017/0071614 A1 | 3/2017 | Vale et al. |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086862 A1 | 3/2017 | Vale et al. |
| 2017/0086863 A1 | 3/2017 | Brady et al. |
| 2017/0086864 A1 | 3/2017 | Greenhalgh et al. |
| 2017/0086996 A1 | 3/2017 | Peterson et al. |
| 2017/0239447 A1 | 3/2017 | Greenhalgh et al. |
| 2017/0095138 A1 | 4/2017 | Nakade et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo et al. |
| 2017/0105743 A1* | 4/2017 | Vale ............... A61B 17/22032 |
| 2017/0112515 A1 | 4/2017 | Brady et al. |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172554 A1 | 6/2017 | Bortlein et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0238953 A1 | 8/2017 | Yang et al. |
| 2017/0252043 A1 | 9/2017 | Fuller et al. |
| 2017/0252064 A1 | 9/2017 | Staunton |
| 2017/0259042 A1 | 9/2017 | Nguyen et al. |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Sethna |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |

(56) References Cited

U.S. PATENT DOCUMENTS

| | | |
|---|---|---|
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2018/0008407 A1 | 1/2018 | Maimon et al. |
| 2018/0042623 A1 | 2/2018 | Batiste |
| 2018/0193050 A1 | 7/2018 | Hawkins et al. |
| 2018/0193591 A1 | 7/2018 | Jaroch et al. |
| 2018/0235743 A1 | 8/2018 | Farago et al. |
| 2018/0256177 A1 | 9/2018 | Cooper et al. |
| 2018/0303610 A1 | 10/2018 | Anderson |
| 2019/0021755 A1 | 1/2019 | Johnson et al. |
| 2019/0021759 A1 | 1/2019 | Krolik et al. |
| 2019/0029820 A1 | 1/2019 | Zhou et al. |
| 2019/0029825 A1 | 1/2019 | Fitterer et al. |
| 2019/0046219 A1 | 2/2019 | Marchand et al. |
| 2019/0192175 A1 | 6/2019 | Chida et al. |
| 2019/0209206 A1 | 7/2019 | Patel et al. |
| 2019/0216476 A1 | 7/2019 | Barry et al. |
| 2019/0239907 A1 | 8/2019 | Brady et al. |
| 2019/0247627 A1 | 8/2019 | Korkuch et al. |
| 2019/0255290 A1 | 8/2019 | Snyder et al. |
| 2019/0269491 A1 | 9/2019 | Jalgaonkar et al. |
| 2019/0274810 A1 | 9/2019 | Phouasalit et al. |
| 2019/0298396 A1 | 10/2019 | Gamba et al. |
| 2019/0365411 A1 | 12/2019 | Avneri et al. |
| 2019/0366049 A1 | 12/2019 | Hannon et al. |
| 2020/0038628 A1 | 2/2020 | Chou et al. |
| 2020/0214859 A1 | 7/2020 | Sherburne |
| 2020/0281611 A1 | 9/2020 | Kelly et al. |
| 2020/0353208 A1 | 11/2020 | Merhi et al. |
| 2020/0383698 A1 | 12/2020 | Miao et al. |
| 2021/0085935 A1 | 3/2021 | Fahey et al. |
| 2021/0153883 A1 | 5/2021 | Casey et al. |
| 2021/0153884 A1 | 5/2021 | Casey et al. |
| 2021/0154433 A1 | 5/2021 | Casey et al. |
| 2021/0219821 A1 | 7/2021 | Appling et al. |
| 2022/0117614 A1 | 4/2022 | Salmon et al. |
| 2022/0125450 A1* | 4/2022 | Sirhan ................... A61B 17/22 |
| 2022/0313426 A1 | 10/2022 | Gifford, III et al. |
| 2023/0054898 A1 | 3/2023 | Gurovich et al. |

FOREIGN PATENT DOCUMENTS

| | | |
|---|---|---|
| CN | 103071195 A | 5/2013 |
| CN | 104507380 A | 4/2015 |
| CN | 104905873 A | 9/2015 |
| CN | 105007973 A | 10/2015 |
| CN | 105307582 A | 2/2016 |
| CN | 105726163 A | 7/2016 |
| CN | 106232059 A | 12/2016 |
| CN | 113040865 A | 6/2021 |
| DE | 20 2009 001 951 U1 | 4/2010 |
| DE | 10 2009 056 450 A1 | 6/2011 |
| DE | 10 2010 010 849 A1 | 9/2011 |
| DE | 10 2010 014 778 A1 | 10/2011 |
| DE | 10 2010 024 085 A1 | 12/2011 |
| DE | 10 2011 014 586 B3 | 9/2012 |
| DE | 20 2020 107013 U1 | 1/2021 |
| EP | 2301450 A1 | 3/2011 |
| EP | 2628455 A1 | 8/2013 |
| EP | 3302312 A1 | 4/2018 |
| EP | 3335647 A2 | 6/2018 |
| EP | 3 420 978 A1 | 1/2019 |
| EP | 4049704 A2 | 8/2022 |
| GB | 2498349 A | 7/2013 |
| JP | 9-19438 A | 1/1997 |
| NO | 2006/021407 A2 | 3/2006 |
| WO | WO 93/04722 A2 | 3/1993 |
| WO | 94/24926 A1 | 11/1994 |
| WO | 97/27808 A1 | 8/1997 |
| WO | 97/38631 A1 | 10/1997 |
| WO | 99/20335 A1 | 4/1999 |
| WO | 99/56801 A2 | 11/1999 |
| WO | 99/60933 A1 | 12/1999 |
| WO | 01/21077 A1 | 3/2001 |
| WO | 02/02162 A2 | 1/2002 |
| WO | 02/11627 A2 | 2/2002 |
| WO | 02/43616 A2 | 6/2002 |
| WO | 02/070061 A1 | 9/2002 |
| WO | 02/094111 A2 | 11/2002 |
| WO | 03/002006 A1 | 1/2003 |
| WO | 03/018085 A2 | 3/2003 |
| WO | 03/030751 A1 | 4/2003 |
| WO | 03/051448 A2 | 6/2003 |
| WO | 2004/028571 A1 | 4/2004 |
| WO | 2004/056275 A1 | 7/2004 |
| WO | 2005/000130 A1 | 1/2005 |
| WO | 2005/027779 A2 | 3/2005 |
| WO | WO 2005/027751 A1 | 3/2005 |
| WO | 2006/031410 A2 | 3/2006 |
| WO | 2006/107641 A2 | 10/2006 |
| WO | 2006/135823 A2 | 12/2006 |
| WO | 2007/054307 A2 | 5/2007 |
| WO | 2007/068424 A2 | 6/2007 |
| WO | 2008/034615 A2 | 3/2008 |
| WO | 2008/051431 A1 | 5/2008 |
| WO | 2008/131116 A1 | 10/2008 |
| WO | WO 2009/019664 A1 | 2/2009 |
| WO | 2009/031338 A1 | 3/2009 |
| WO | 2009/076482 A1 | 6/2009 |
| WO | 2009/086482 A2 | 7/2009 |
| WO | 2009/105710 A1 | 8/2009 |
| WO | WO 2009/103125 A1 | 8/2009 |
| WO | 2010/010545 A1 | 1/2010 |
| WO | 2010/046897 A1 | 4/2010 |
| WO | 2010/075565 A1 | 7/2010 |
| WO | 2010/102307 A1 | 9/2010 |
| WO | 2010/146581 A1 | 12/2010 |
| WO | 2011/013556 A1 | 2/2011 |
| WO | 2011/066961 A1 | 6/2011 |
| WO | 2011/082319 A1 | 7/2011 |
| WO | 2011/095352 A1 | 8/2011 |
| WO | 2011/106426 A1 | 9/2011 |
| WO | 2011/110316 A1 | 9/2011 |
| WO | 2012/052982 A1 | 4/2012 |
| WO | 2012/064726 A1 | 5/2012 |
| WO | 2012/081020 A1 | 6/2012 |
| WO | 2012/110619 A1 | 8/2012 |
| WO | 2012/120490 A2 | 9/2012 |
| WO | 2012/156924 A1 | 11/2012 |
| WO | 2013/016435 A1 | 1/2013 |
| WO | 2013/072777 A2 | 5/2013 |
| WO | 2013/105099 A2 | 7/2013 |
| WO | 2013/109756 A2 | 7/2013 |
| WO | 2014/081892 A1 | 5/2014 |
| WO | 2014/139845 A1 | 9/2014 |
| WO | 2014/169266 A1 | 10/2014 |
| WO | 2014/178198 A1 | 11/2014 |
| WO | WO 2014/188300 A1 | 11/2014 |
| WO | 2015/061365 A1 | 4/2015 |
| WO | 2015/134625 A1 | 9/2015 |
| WO | 2015/179324 A2 | 11/2015 |
| WO | WO 2015/179377 A1 | 11/2015 |
| WO | 2015/189354 A1 | 12/2015 |
| WO | 2016/010995 A1 | 1/2016 |
| WO | WO 2017/004234 A1 | 1/2017 |
| WO | WO 2017/097616 A1 | 6/2017 |
| WO | 2018/193603 A1 | 10/2018 |
| WO | WO 2018/178979 A1 | 10/2018 |
| WO | WO 2019/064306 A1 | 4/2019 |
| WO | WO 2019/079296 A1 | 4/2019 |
| WO | WO 2020/139979 A1 | 7/2020 |
| WO | WO 2021/016213 A1 | 1/2021 |

(56) References Cited

FOREIGN PATENT DOCUMENTS

WO  WO 2021/167653 A1  8/2021
WO  WO 2022/020366 A2  1/2022

OTHER PUBLICATIONS

Struffert, T., et al. "Intravenous flat detector CT angiography for non-invasive visualisation of intracranial flow diverter: technical feasibility" Eur Radiol 21:1797-1801 (2011).

Extended European Search Report issued in corresponding EP Application No. 21 16 5800 dated Oct. 27, 2021.

* cited by examiner

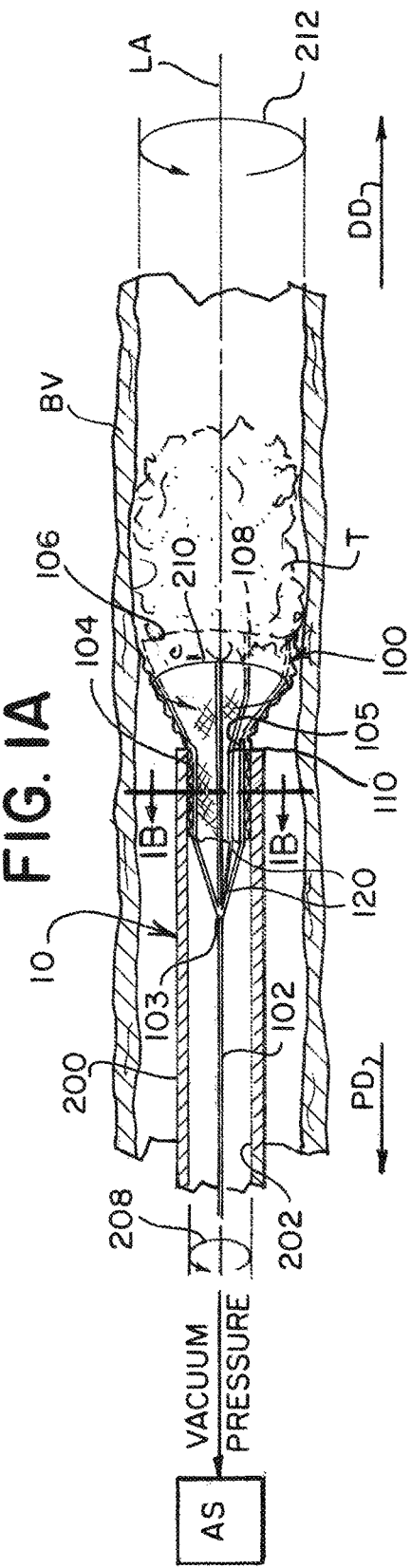
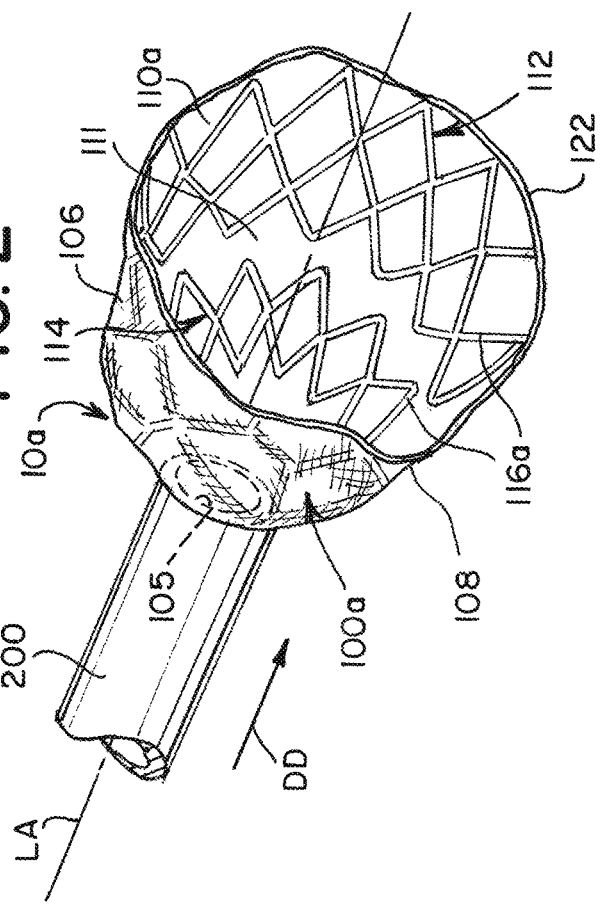
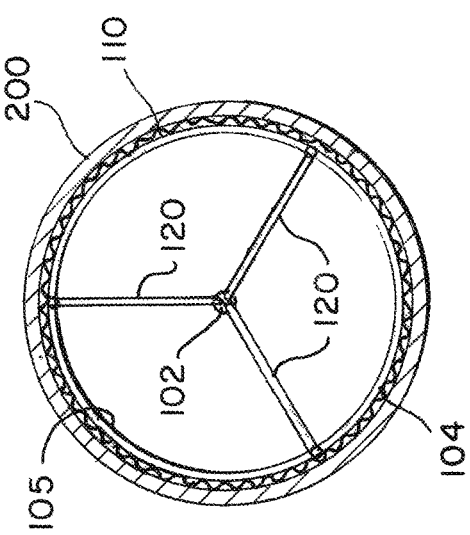

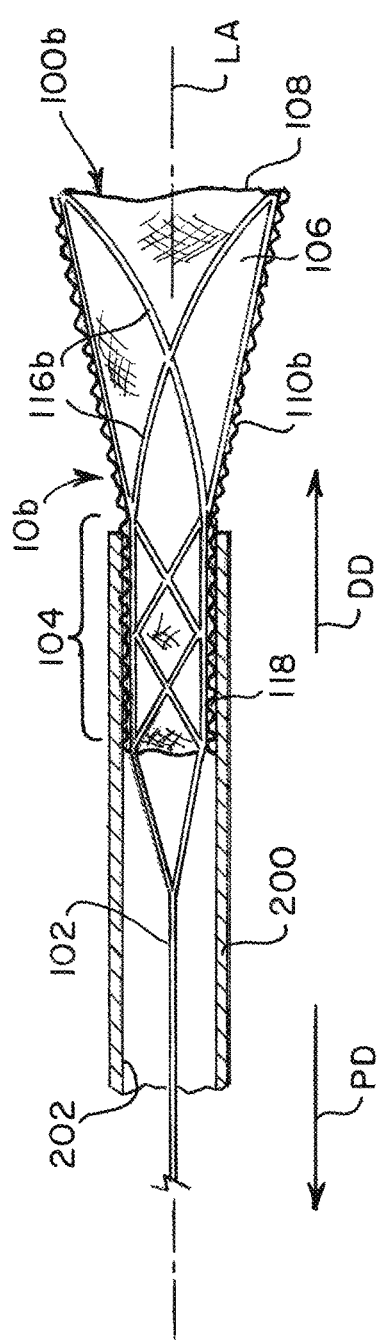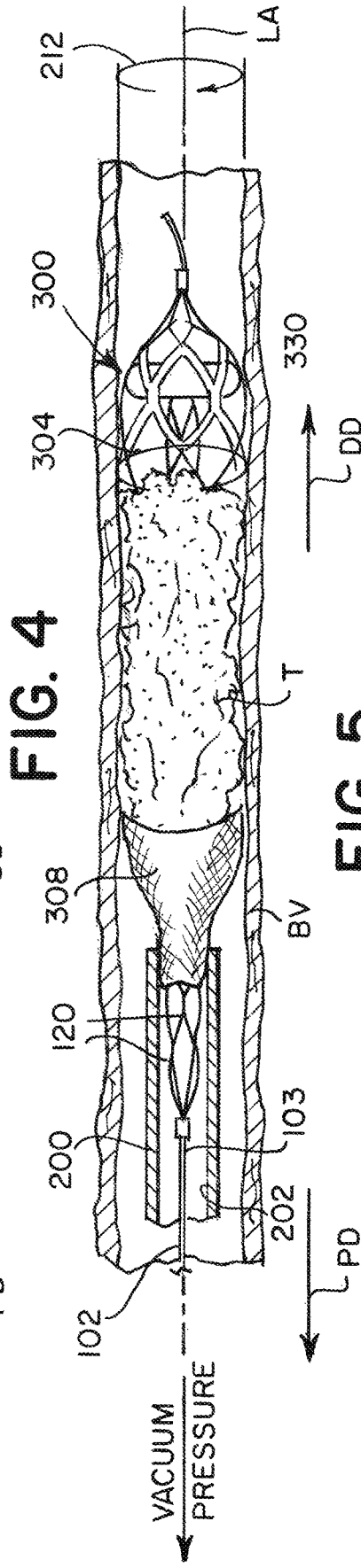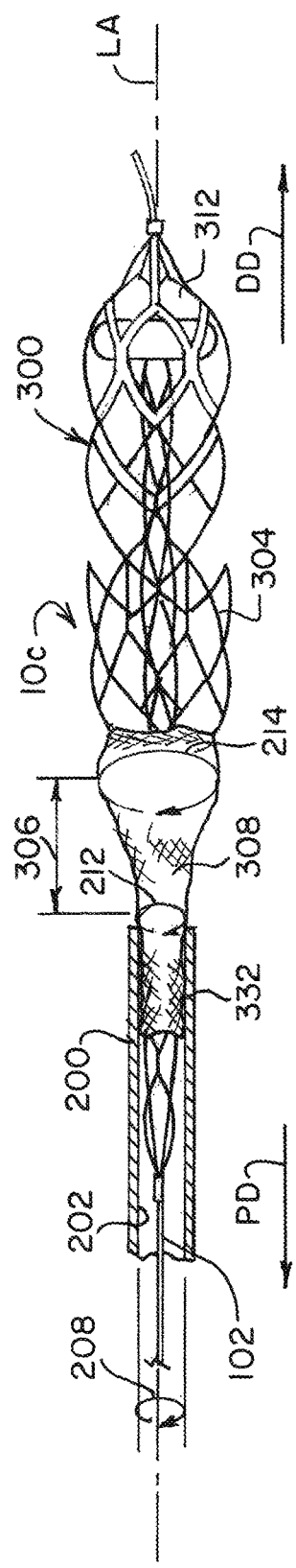

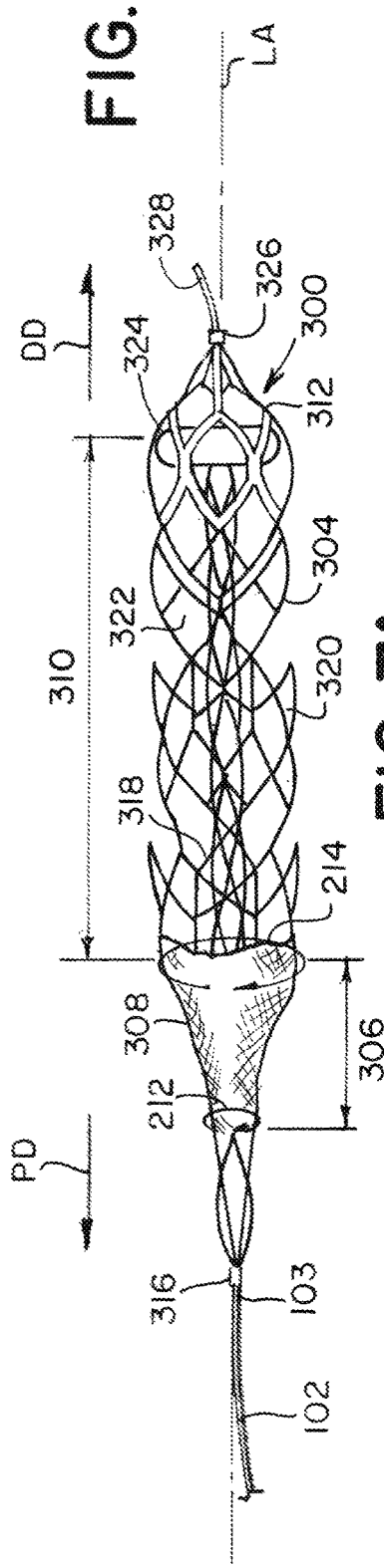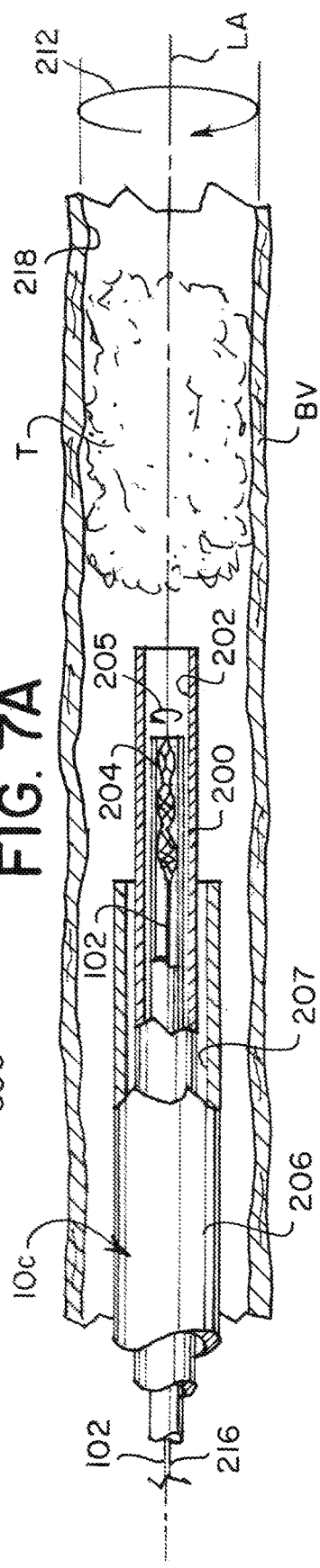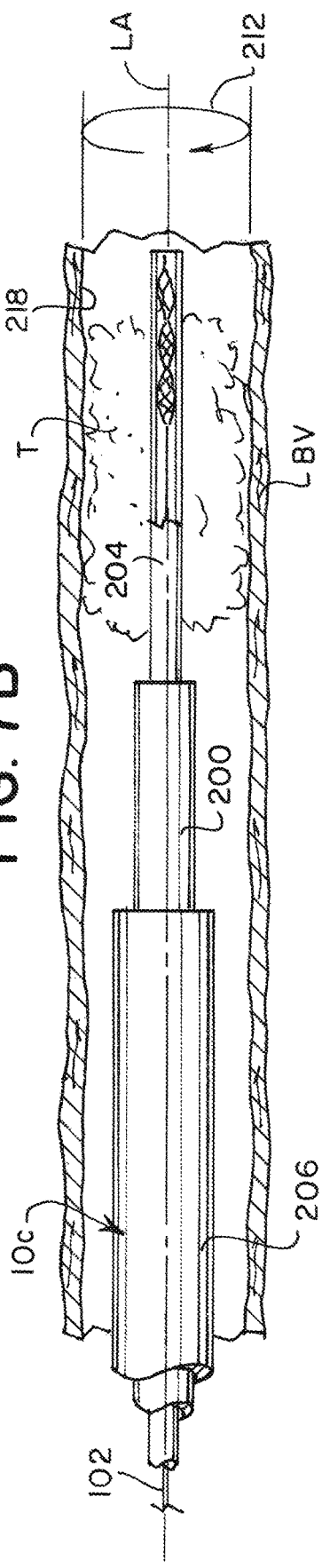

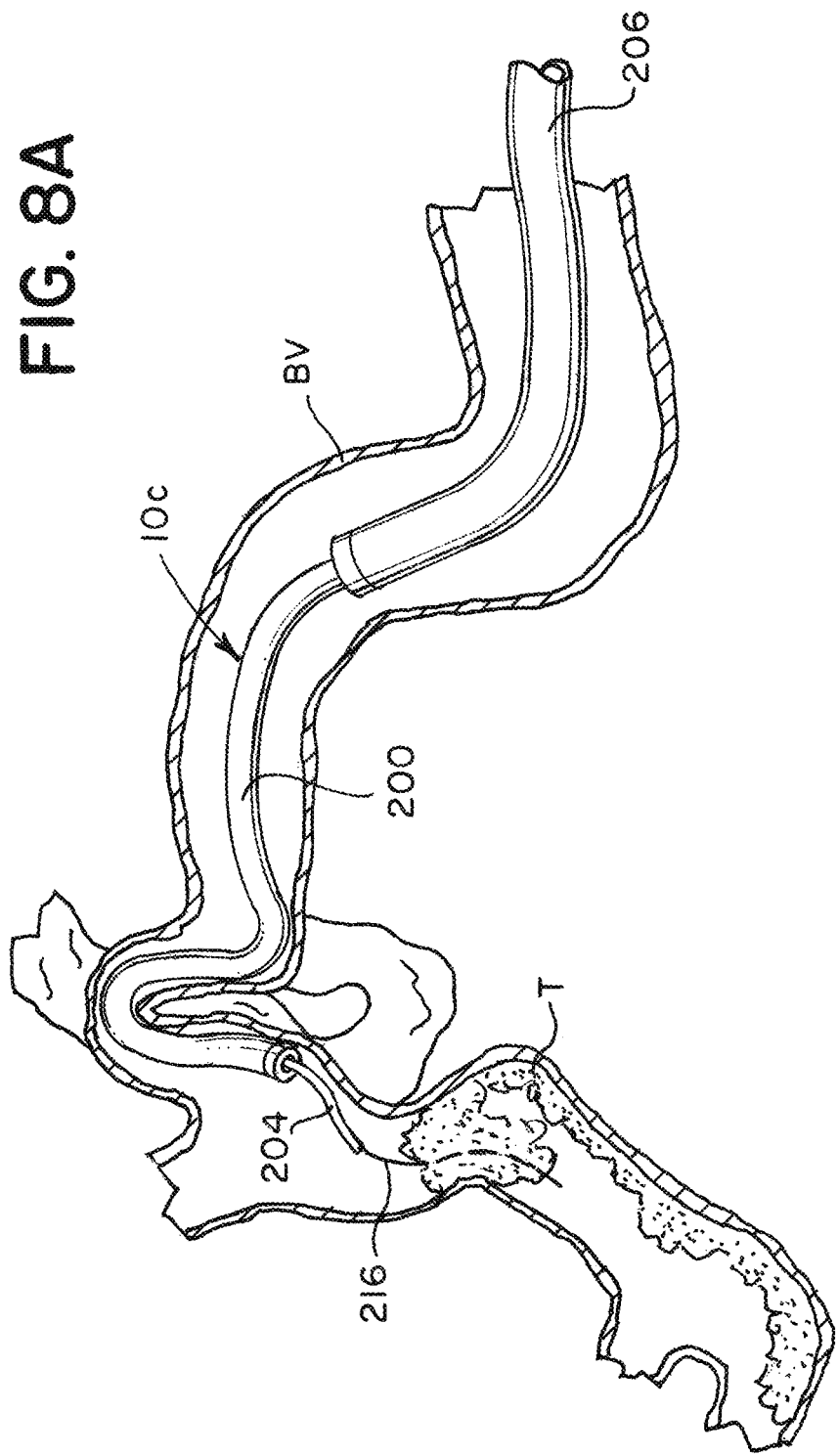

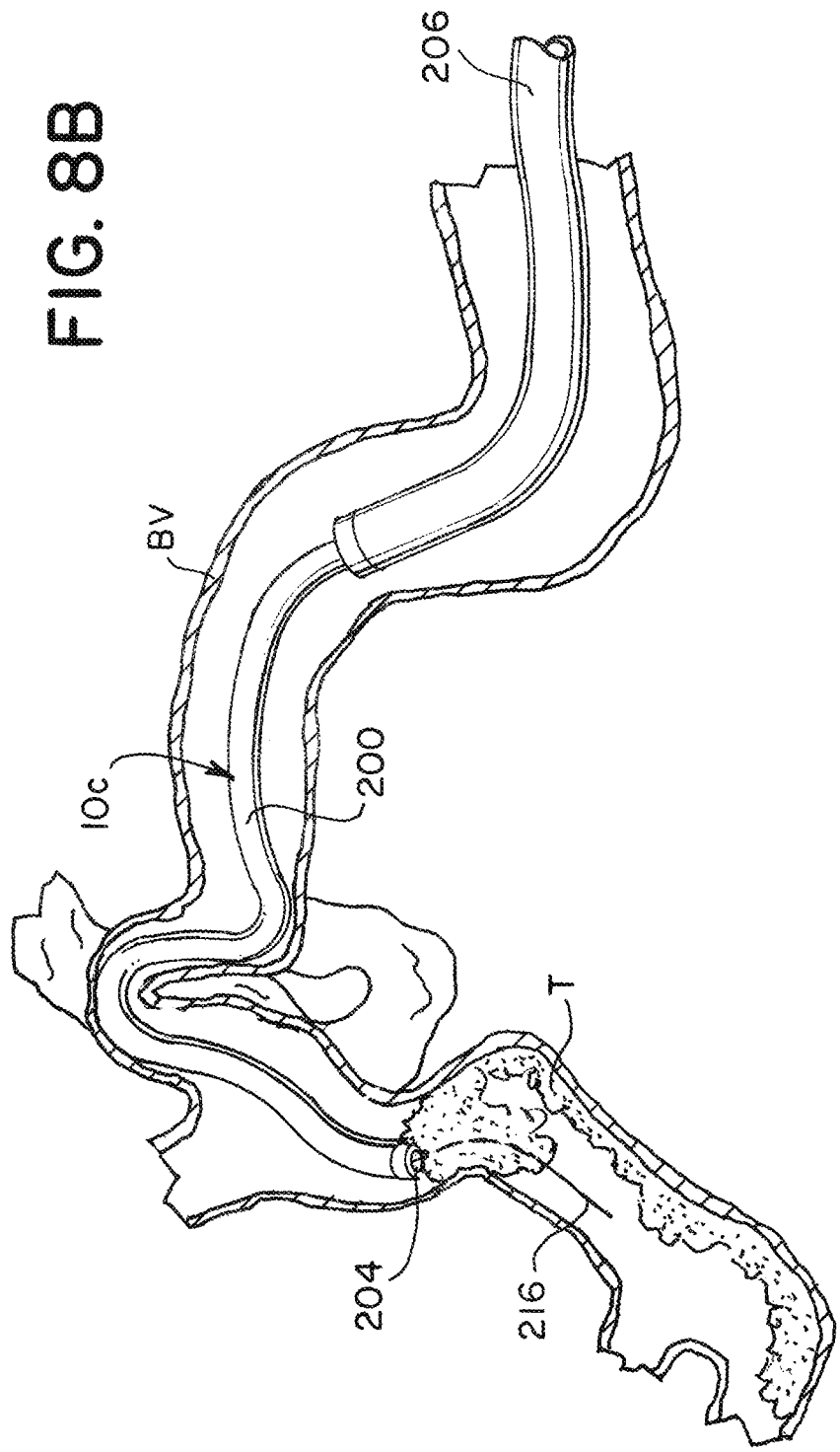

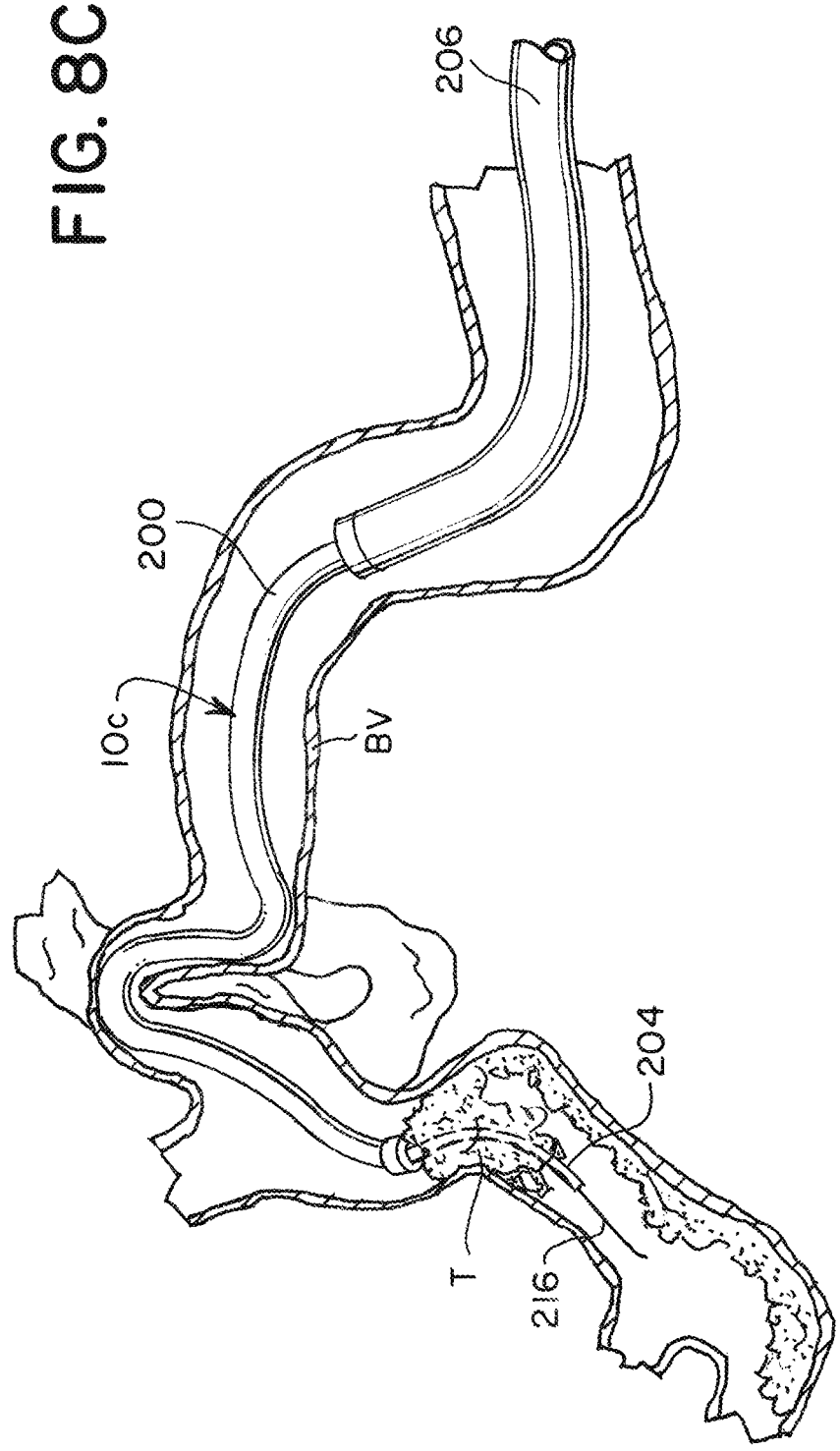

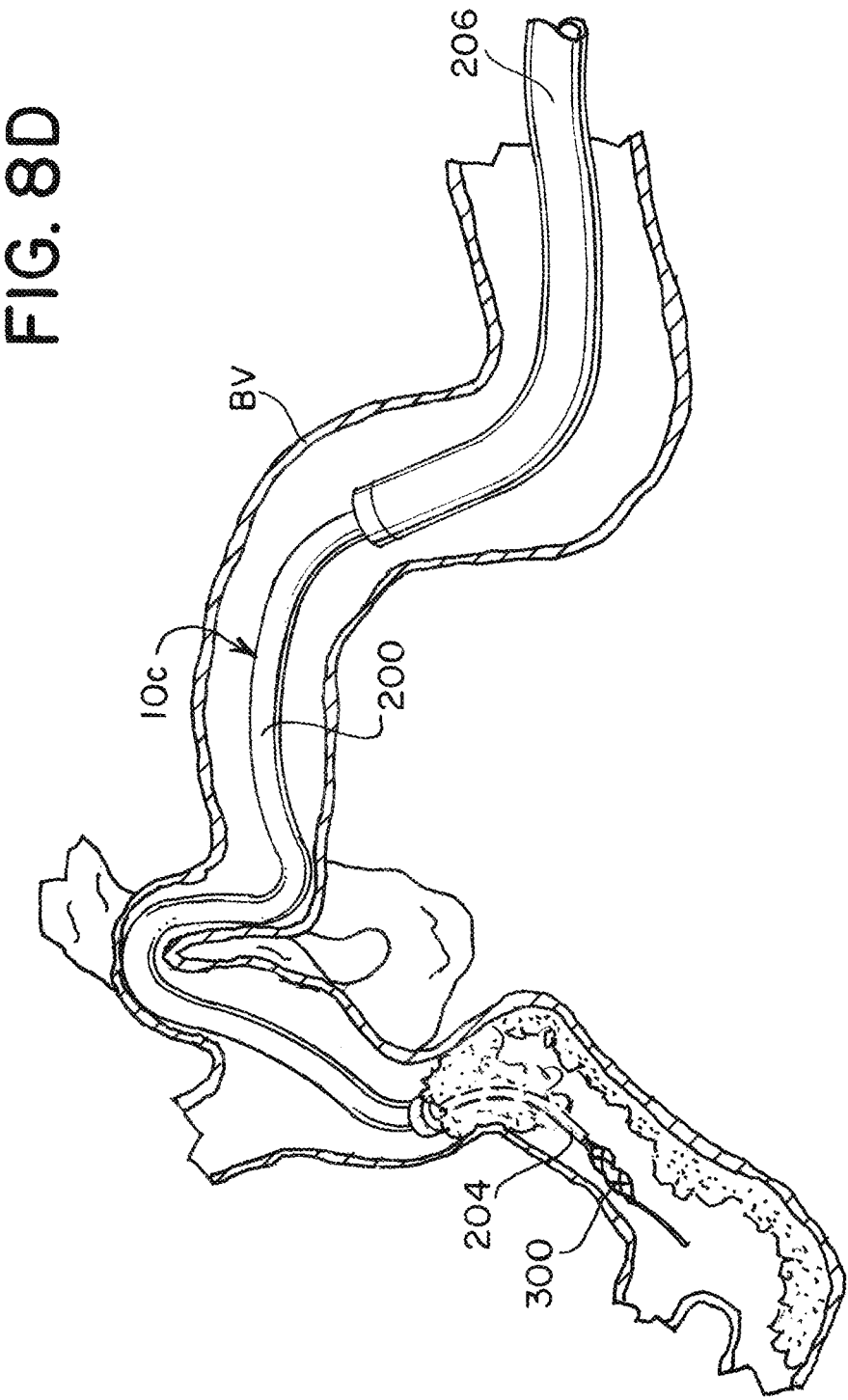

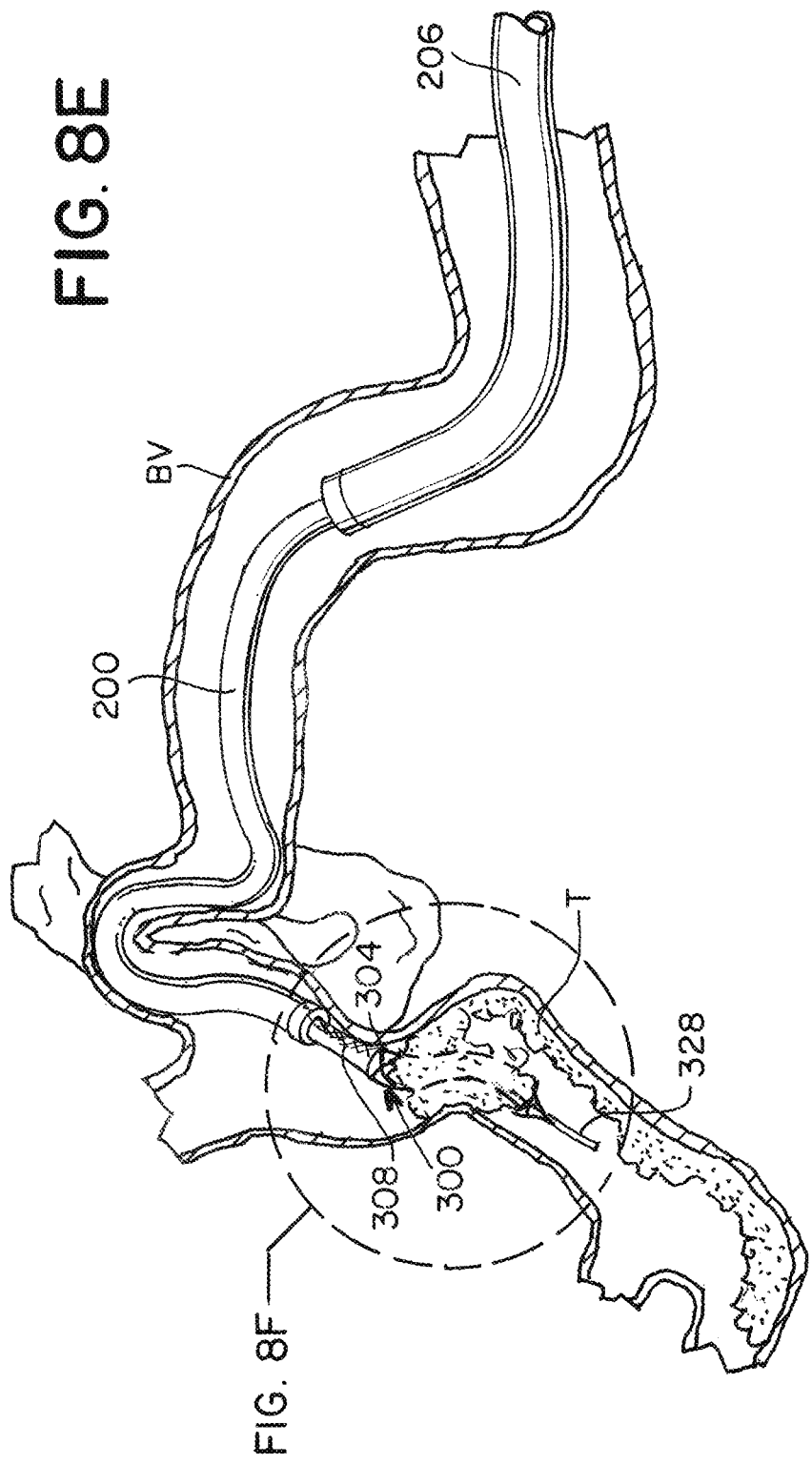

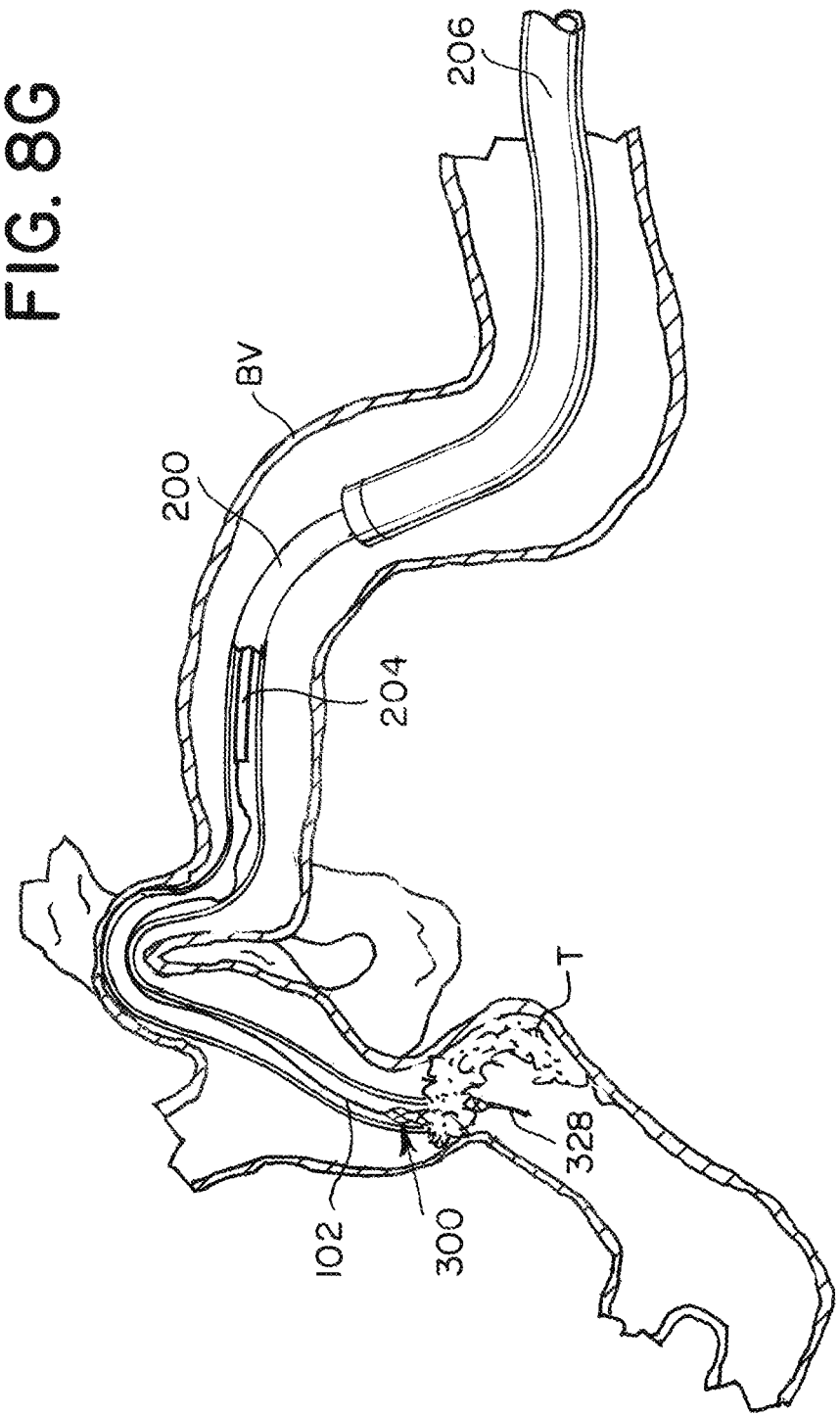

FIG. 9A

| Commercial Product | Pump System | Distal Internal Diameter (inch) | Maximum Vacuum Pressure (inHg) | Maximum Vacuum Pressure (Pa) | Tip Cross Section Area (inch²) | Tip Cross Section Area (m²) | Force at Tip at Maximum Vacuum Pressure (N) | Force at Tip at Maximum Vacuum Pressure (gf) |
|---|---|---|---|---|---|---|---|---|
| A | Engine | 0.071 | 29.2 | 98882.3 | 0.003959 | 2.554E-06 | 0.253 | 25.8 |
| B | Engine | 0.068 | 29.2 | 98882.3 | 0.003632 | 2.343E-06 | 0.232 | 23.6 |
| C | Engine | 0.072 | 29.2 | 98882.3 | 0.004072 | 2.627E-06 | 0.260 | 26.5 |
| D | Gomco | 0.070 | 25 | 84659.5 | 0.003848 | 2.483E-06 | 0.210 | 21.4 |
| E | Zenith | 0.071 | 26.6 | 90077.7 | 0.004301 | 2.554E-06 | 0.230 | 23.5 |
| F | Zenith | 0.074 | 26.6 | 90077.7 | 0.003959 | 2.775E-06 | 0.250 | 25.5 |
| G | Medela | 0.068 | 28 | 94818.6 | 0.003632 | 2.343E-06 | 0.222 | 22.7 |
| H | Riptide | 0.068 | 29 | 98205.0 | 0.003632 | 2.343E-06 | 0.230 | 23.5 |
| I | Riptide | 0.071 | 29 | 98205.0 | 0.003959 | 2.554E-06 | 0.251 | 25.6 |
| Funnel Tip | Engine | 0.157 | 29.2 | 98882.3 | 0.030434 | 1.963E-05 | 1.243 | 126.7 |

100a, 100b

Assuming: vessel with internal diameter of 0.157 inch = 4 mm

FIG. 9B

| Commercial Product | Pump System | Distal Internal Diameter (inch) | Maximum Vacuum Pressure (inHg) | Maximum Vacuum Pressure (Pa) | Tip Cross Section Area (inch²) | Tip Cross Section Area (m²) | Force at Tip at Maximum Vacuum Pressure (N) | Force at Tip at Maximum Vacuum Pressure (gf) |
|---|---|---|---|---|---|---|---|---|
| A | Engine | 0.071 | 29.2 | 98882.3 | 0.003959 | 2.554E-06 | 0.253 | 25.8 |
| B | Engine | 0.068 | 29.2 | 98882.3 | 0.003632 | 2.343E-06 | 0.232 | 23.6 |
| C | Engine | 0.072 | 29.2 | 98882.3 | 0.004072 | 2.627E-06 | 0.260 | 26.5 |
| D | Gomco | 0.070 | 25 | 84659.5 | 0.003848 | 2.483E-06 | 0.210 | 21.4 |
| E | Zenith | 0.071 | 26.6 | 90077.7 | 0.004301 | 2.554E-06 | 0.230 | 23.5 |
| F | Zenith | 0.074 | 26.6 | 90077.7 | 0.003959 | 2.775E-06 | 0.250 | 25.5 |
| G | Medela | 0.068 | 28 | 94818.6 | 0.003632 | 2.343E-06 | 0.222 | 22.7 |
| H | Riptide | 0.068 | 29 | 98205.0 | 0.003632 | 2.343E-06 | 0.230 | 23.5 |
| I | Riptide | 0.071 | 29 | 98205.0 | 0.003959 | 2.554E-06 | 0.251 | 25.6 |
| Stent Funnel | Engine | 0.157 | 29.2 | 98882.3 | 0.030434 | 1.963E-05 | 1.243 | 126.7 |

Assuming: vessel with internal diameter of 0.177 inch = 4 mm

300

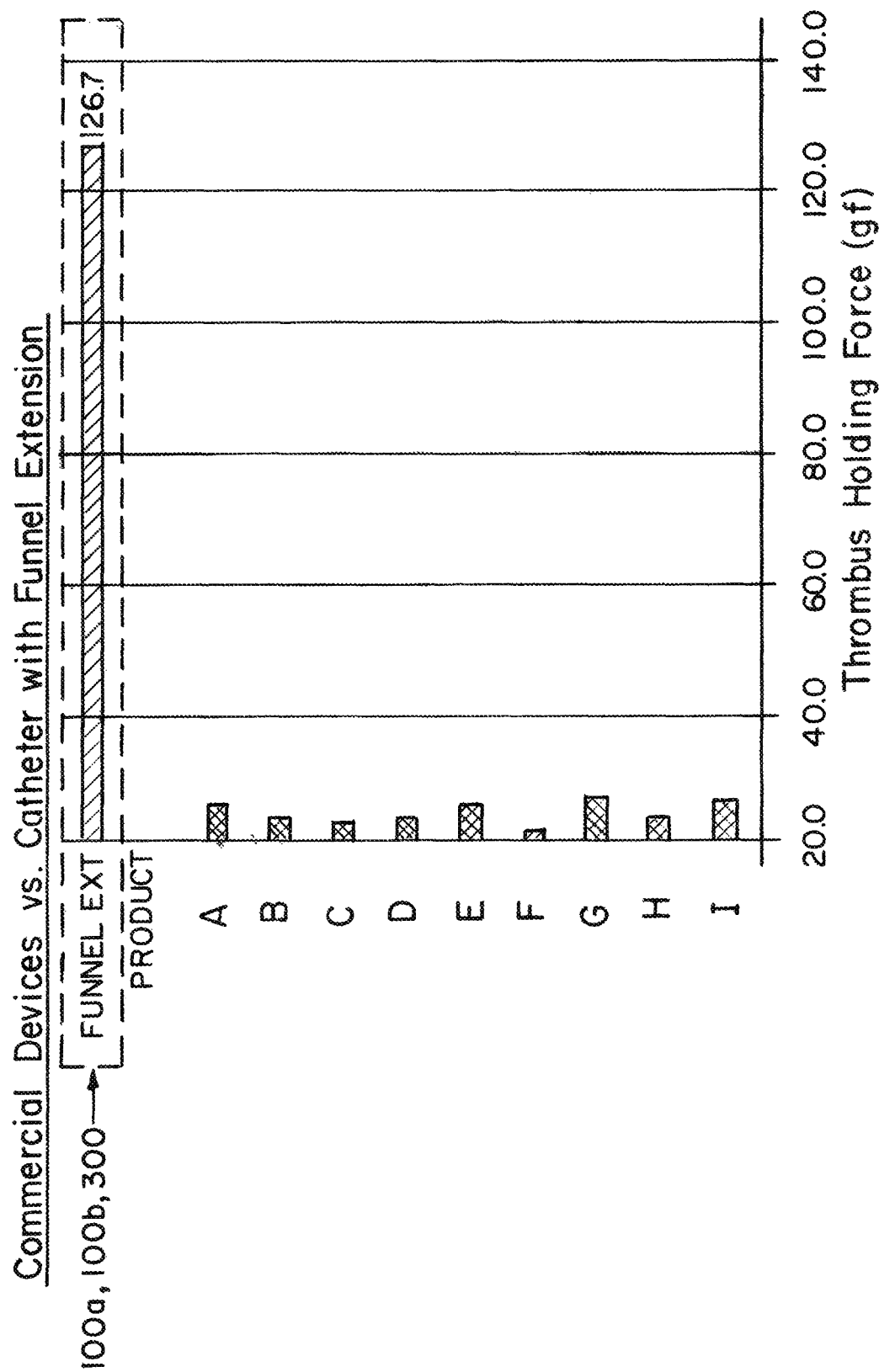

CATHETER FUNNEL EXTENSION

FIELD OF INVENTION

The present invention generally relates to systems and methods for removing acute blockages from blood vessels during intravascular medical treatments.

BACKGROUND

Clot retrieval catheters and devices are used in mechanical thrombectomy for endovascular intervention, often in cases where patients are suffering from conditions such as acute ischemic stroke (AIS), myocardial infarction (MI), and pulmonary embolism (PE). The immediate hours after these life-threatening events are critical, as a clot that occurs within a blood vessel must be removed as soon as possible to prevent long term disability, brain damage, or death. Accessing the neurovascular bed can be challenging with conventional technology, as the target vessels are small in diameter, remote relative to the site of insertion, and highly tortuous. Traditional devices are often either too large in profile, lack the deliverability and flexibility needed to navigate tortuous vessels, or are not entirely effective at removing a clot when delivered to the target site. Further, tissue plasminogen activator ("tPA") has been the traditional, FDA-approved treatment for removing blood clots in the brain; however, when the blood clot is in a major blood vessel, tPA can become less effective. This drawback has stimulated the need for a device that can effectively and quickly remove blood clots in major blood vessels.

The clot itself can additionally complicate procedures by embodying a number of complex morphologies and consistencies, ranging from simple tube-shaped structures which assume the shape of the vessel to long, strand-like arrangements that can span multiple vessels at one time. The age of a clot can also affect its compliance, with older clots tending to be less compressible than fresh clots. Experience has also demonstrated that depending on the nature of the interaction with a clot retrieval device, the mechanical properties of a clot can be affected in a significant way. Additionally, several mechanisms can play a role in strongly adhering the clot to the vessel wall. Breaking these bonds without damaging fragile neurovascular vessels can be a significant challenge.

The delivery of effective devices to the small and highly-branched cerebral artery system remains challenging, and conventional clot retrieval devices can suffer from a number of drawbacks. The retrieval device must also be sufficiently flexible to navigate the vasculature and endure high strains, while also having the axial stiffness to offer smooth advancement along the route. Once at the target site, typical objects to be retrieved from the body are substantially larger in size than the device, making it more difficult to retrieve objects into the tip. For example, firm, fibrin-rich clots can often be difficult to extract as they can become lodged in the tip of traditional fixed-mouth catheters and devices. Additionally, this lodging can cause softer portions to shear away from the firmer regions of the clot.

Small diameters and fixed tip sizes are also less efficient at directing the aspiration necessary to remove blood and thrombus material during the procedure. The suction must be strong enough such that any fragmentation that can occur as a result of aspiration or the use of a mechanical thrombectomy device can be held stationary so that fragments cannot migrate and occlude distal vessels. However, when aspirating with a fixed-mouth catheter or device, a significant portion of the aspiration flow ends up coming from vessel fluid proximal to the tip of the catheter or device, where there is no clot. This can significantly reduce aspiration efficiency, lowering the success rate of clot removal.

Applicants therefore recognize a need for improved methods, devices, and systems that can incorporate an expansile funnel that deploys outside a catheter, allowing for effective and quick retrieval of blood clots due to the greater thrombus removal force resulting from the increased area engaging the thrombus. Additionally, there is a need for improved methods, devices, and systems that incorporate a stent retriever having an expandable framework that functions as a funnel catheter tip extension to provide effective and quick retrieval of blood clots.

SUMMARY

Generally, system for retrieving a blood clot in a blood vessel using a clot retrieval device having an expansile funnel that can engage with the blood clot is provided. The present disclosure also includes a clot retrieval device having an expandable framework that can engage with the blood clot. The expansile funnel and expandable framework can expand from a collapsed delivery state to an expanded deployed state, increasing the cross-sectional area of the clot retrieval device engaging the blood clot. The increased cross-sectional area of the clot retrieval device can increase the aspiration suction force, providing effective removal of the clot from the patient.

An example system for retrieving an obstruction in a blood vessel can include an outer catheter facilitating the introduction of microcatheters, guidewires, or any of a number of commercially available products to a target site within the vasculature. The outer catheter can be one or both of a guide catheter and an intermediate catheter. Within the outer catheter can be a clot retrieval device. The clot retrieval device can include an elongate flexible delivery wire having a distal end; an expansile tube having a lumen and being affixed to the distal end of the elongated flexible wire; and an expansile funnel affixed to the expansile tube. The expansile funnel can be expandable from a collapsed delivery state, in which the expansile funnel can have a circumference approximately the size of the lumen of the outer catheter, to an expanded deployed state, in which the expansile funnel can have a circumference greater than the circumference of the lumen of the outer catheter. The expansile funnel can include a fluid-impermeable flexible tube; an open distal mouth at the distal end of the flexible tube; and a first and second ring of struts affixed to and structurally supported by the flexible tube. The fluid-impermeable flexible tube can include a lumen in fluid communication with the lumen of the expansile funnel. The second ring of struts can be positioned proximal to the first ring of struts. An aspiration source can be attached to the system to apply suction through a fluidic passage of the outer catheter and the clot retrieval device.

When the expansile funnel is in the expanded deployed state, approximately half of the clot retrieval device can be positioned within the lumen of the outer catheter, while approximately half of the clot retrieval device can be positioned within a blood vessel.

When the expansile funnel is in the expanded deployed state and the expansile tube is positioned within the lumen of the outer catheter, the outer walls of the expansile tube can form a seal against the lumen of the outer catheter.

When the expansile funnel is in the expanded deployed state, the expansile funnel can expand to circumferentially appose a lumen of the blood vessel.

When the expansile funnel is in the collapsed delivery state, a portion of the expansile funnel and the expansile tube can have common circumferential dimensions.

When the expansile funnel is in the collapsed delivery state and is positioned within the lumen of the outer catheter, the lumen of the flexible tube, the lumen of the expansile tube, and the lumen of the outer catheter can be aligned coaxially about a longitudinal axis.

The fluid-impermeable flexible tube can provide the sole structural support for the expansile funnel between the first and second ring of struts. The fluid-impermeable flexible tube can be stitched and/or adhered to the first ring of struts and the second ring of struts. The fluid-impermeable flexible tube can include flexible polymer material.

Another example system can include an outer catheter facilitating the introduction of microcatheters, guidewires, or any of a number of commercially available products to a target site within the vasculature. The outer catheter can be one or both of a guide catheter and an intermediate catheter. Within a lumen of the outer catheter can be a stent retriever. The stent retriever can include an elongate flexible delivery wire; an expandable framework; and a fluid-impermeable membrane. The expandable framework can engage and capture the obstruction within a blood vessel by expanding from a collapsed delivery configuration to an expanded deployed configuration. A proximal end of the expandable framework can be attached to a distal end of the delivery wire. The expandable framework can include a tubular portion that can have an elongated tubular shape when expanded. The expandable framework can taper proximally from the tubular portion to the distal end of the delivery wire. The fluid-impermeable membrane can be affixed to the expandable framework near the proximal end of the framework such that the fluid-impermeable membrane has a funnel shape when the expandable framework is in the expanded configuration.

The tubular portion of the expandable framework can have multiple cell openings sized to pass through the obstruction when the expandable framework expands from the collapsed delivery configuration.

The system can include the expandable framework including a closed distal end portion extending distally away from the tubular portion of the framework and radially inward towards a central axis.

The tubular portion can be expandable to have approximately the same circumference as the circumference of the blood vessel when the expandable framework is in the expanded deployed configuration, allowing for complete engagement with the obstruction.

The system can include a microcatheter sized to traverse the lumen of the outer catheter. The expandable framework can be sized to traverse a lumen of the microcatheter when in the collapsed delivery state.

When deployed a blood vessel as part of a treatment, the fluid-impermeable membrane can include a first outer circumference approximately equal to an inner circumference of the lumen of the outer catheter and a second outer circumference approximately equal to the inner circumference of the blood vessel. When the expandable framework is in the expanded configuration, a portion of the proximal portion of the expanded framework can be positioned within the lumen of the outer catheter. This configuration can provide an outer force on the lumen of the outer catheter such that a fluid-impermeable seal is created between the fluid-impermeable membrane and the lumen of the outer catheter. This configuration can further provide a force between the fluid impermeable membrane and the walls of the blood vessel such that a fluid-impermeable seal is created between the fluid-impermeable membrane and the walls of the blood vessel.

An example method for retrieving an obstruction from a blood vessel can include one or more of the following steps presented in no particular order. The example method can include additional steps as would be appreciated and understood by a person of ordinary skill in the art. The example method can be performed by an example system as disclosed herein, a variation thereof, or an alternative thereto as would be appreciated and understood by a person of ordinary skill in the art.

The method can include accessing an arterial blood vessel of a patient using an outer catheter; positioning a distal end of the outer catheter proximate to the obstruction; advancing a microcatheter and an expandable framework having a fluid-impermeable membrane, in a collapsed delivery state, through the lumen of the outer catheter; crossing the obstruction with the microcatheter and the expandable framework in the collapsed configuration; retracting the microcatheter into the lumen of the outer catheter while the expandable framework maintains contact with the obstruction; expanding a portion of the expandable framework through the obstruction; expanding a distal portion and proximal portion of the membrane to circumferentially appose the lumen of the outer catheter; and aspirating through a fluidic passage.

The method can include advancing the outer catheter to a distance approximately three millimeters away from the obstruction.

The method can include retracting a portion of the expandable framework into the lumen of the outer catheter while aspirating resulting in removing the expandable framework with the obstruction from the patient.

The method can include injecting contrast media within the lumen of the outer catheter to assess the degree of obstruction remaining in the blood vessel.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation. It is expected that those of skill in the art can conceive of and combining elements from multiple figures to better suit the needs of the user.

FIG. 1A is an illustration of a system for retrieving an obstruction using an expansile funnel, according to aspects of the present invention.

FIG. 1B is an illustration of a cross-sectional view of the interior of the expansile tube in FIG. 1A, according to aspects of the present invention.

FIG. 2 is an illustration of an expansile funnel including a first and second ring of struts, according to aspects of the present invention.

FIG. 3 shows a view of the system for retrieving an obstruction using an expansile funnel including a fluid-impermeable flexible tube, according to aspects of the present invention.

FIG. 4 is an illustration of a system for retrieving an obstruction using a stent retriever according to aspects of the present invention.

FIG. 5 shows a view of the system including a fluid-impermeable membrane and expandable framework on the stent retriever, according to aspects of the present invention.

FIG. 6 is an illustration of a stent retriever with a fluid-impermeable membrane, according to aspects of the present invention.

FIGS. 7A-7D are a series of views of the deployment of a stent retriever to remove an obstruction from a blood vessel according to aspects of the present invention.

FIGS. 8A-8H are a series of views of the method of removing an obstruction from a blood vessel using a first catheter, outer catheter, microcatheter, and stent retriever according to aspects of the present invention.

FIGS. 9A-9B illustrate the increased obstruction removal force provided by the disclosed technology compared to the obstruction removal force provided by commercially available products, according to aspects of the present invention.

FIG. 10 graphically depicts the obstruction removal force provided by the disclosed technology compared to the obstruction removal forced provided by commercially available products, according to aspects of the present invention.

DETAILED DESCRIPTION

Figure 7C:
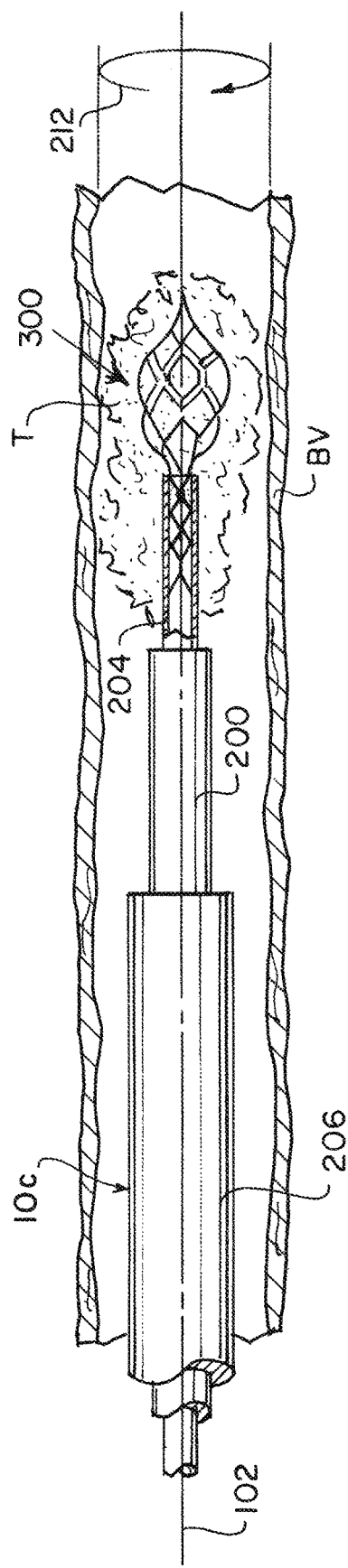

Specific examples of the present invention are now described in detail with reference to the Figures, where identical reference numbers indicate elements which are functionally similar or identical.

A key success factor in intravascular treatment such as aneurysm treatments relates to the obstruction removal force defined as the product of the vacuum pressure times the catheter cross sectional area. In some treatments, mechanical clot removal devices referred to herein generically as "stent retrievers" are also used in combination with aspiration. In order to increase the obstruction removal force, either the vacuum pressure or the catheter cross-sectional area can be increased. The disclosed technology relates to a clot retrieval device including an expansile funnel that can increase the cross-sectional area of the device that can be in contact with the obstruction. Alternatively, the disclosed technology relates to a stent retriever including an expandable framework having a membrane thereon that can provide a sealed opening to the catheter lumen, the sealed opening providing a cross sectional area in contact with the obstruction that is greater than the catheter cross sectional area. Because the cross-sectional area is increased, the obstruction removal force can be increased, resulting in improved removal of an obstruction from a patient compared to suction through the catheter alone.

Accessing the various vessels within the vascular, whether they are coronary, pulmonary, or cerebral, involves well-known procedural steps and the use of a number of conventional, commercially-available accessory products. These products, such as angiographic materials, rotating hemostasis valves, and guidewires are widely used in laboratory and medical procedures. When these products are employed in conjunction with the system and methods of this invention in the description below, their function and exact constitution are not described in detail.

FIG. 1A illustrates a system 10 for retrieving an obstruction (T). FIG. 1B illustrates a cross section of the system 10 as indicated in FIG. 1A. Referring collectively to FIGS. 1A and 1B, the system 10 as illustrated includes a clot retrieval device 100 and an outer catheter 200. The clot retrieval device 100 is slidably translatable within the lumen 202 of the outer catheter 200 and expandable such that a distal funnel 106 portion of the device 100 expands to walls of the blood vessel (BV) and a proximal portion 104 of the device expands to the walls of the lumen 202 of the outer catheter 202 when the distal funnel 106 portion is slid distally to exit the outer catheter 200. The system 10 can be configured to aspirate through the catheter 200 and expanded device 100 to dislodge and/or extract an obstruction (T) including an occlusive clot or thrombus, debris, and/or other foreign mass within a blood vessel (BV) of a patient.

FIG. 2 illustrates an end perspective view of a system 10a including a clot retriever device 100a and an outer catheter 200. The device 100a illustrated in FIG. 2 can be configured to function according to the principles of the device 100 illustrated in FIGS. 1A and 1B. The system 10a illustrated in FIG. 2 can be configured to be positioned within a blood vessel (BV) and retrieve an obstruction (T) similar to the system 10 as illustrated in FIG. 1A. The distal funnel portion 106 of the device 100a as illustrated in FIG. 2 includes a fluid-impermeable flexible tube 110a affixed to a strut framework 116a. The strut framework 116a includes a first, distal ring of struts 112 and a second ring of struts 114 positioned in the proximal direction (PD) in relation to the first ring of struts 112. The first and second ring of struts 112, 114 can be disposed approximate to the open distal mouth 108 of the expansile funnel 106. In some examples, the device 100a can include one or more additional rings of struts positioned in the proximal direction (PD) in relation to the first and second ring of struts 112, 114. In some examples, the strut framework 116a can extend into the lumen 105 of the expansile tube 104. In some examples, the first and second rings of struts 112, 114 are separated such that the flexible tube 110a structurally supports each ring of struts 112, 114. The distal end of the fluid-impermeable flexible tube 110a can define an open distal mouth 108 of the device 100a. In some examples, the cover 110a can be a fluid-impermeable flexible tube fixed to the strut framework 116a. The fluid-impermeable flexible tube 110a can be stitched to the strut framework 116a, as illustrated in FIG. 2.

FIG. 3 illustrates a side view of a system 10b including a clot retriever device 100b and an outer catheter 200. The device 100b illustrated in FIG. 3 can be configured to function according to the principles of the device 100 illustrated in FIGS. 1A and 1B. The system 10b illustrated in FIG. 3 can be configured to be positioned within a blood vessel (BV) and retrieve an obstruction (T) similar to the system 10 as illustrated in FIG. 1A. The expansile tube 104 and distal funnel 106 of the device 100b illustrated in FIG. 3 can include a strut framework 116b and a fluid impermeable tube, coating, or membrane 110b. In contrast to the framework 116a illustrated in FIG. 2, the framework 116b illustrated in FIG. 3 can be contiguous. The framework 116b illustrated in FIG. 3 can be shaped, made of suitable materials, and otherwise constructed to structurally support the fluid-impermeable cover 110b. In some examples, the cover 110b can include a fluid-impermeable flexible tube, and the tube 110b can be adhered to the strut framework 116b. The fluid-impermeable flexible 110 can be adhered to the strut framework 116a by applying heat.

Referring collectively to FIGS. 1A, 1B, 2, and 3 the outer catheter 200 can be sized, constructed, and otherwise configured to navigate the blood vessel (BV) to a treatment site and facilitate introduction of the clot retrieval device 100, 100a, 100b across the obstruction (T). In one example, the outer catheter 200 can be an aspiration catheter. The aspiration catheter can be a rapid-exchange (RX) type. The outer catheter 200 can include a lumen 202 traversing the length of the outer catheter 200. The lumen 202 can be sized to receive a clot retrieval device 100, 100a, 100b and provide sufficient space for the clot retrieval device 100 to move through the lumen 202 along a longitudinal axis as the system 10 approaches and engages with the obstruction (T). The system 10, 10a, 10b can include an aspiration source (AS) that can be configured to apply suction through a fluidic passage within the lumen 202 of the outer catheter 204. The aspiration source (AS) can provide sufficient suction for engaging the clot retrieval device 100, 100a, 100b with an obstruction (T) to effectively remove the obstruction (T) from a blood vessel (BV) of a patient. In one example, the aspiration source (AS) can be first applied to the lumen 202 of the outer catheter 200 and then directed to the expansile funnel 106 of the clot retrieval device 100, 100a, 100b.

The clot retrieval device 100, 100a, 100b can include a flexible delivery member 102 (also referred to herein generically as "delivery wire"), an expansile tube 104, and an expansile funnel 106. The expansile tube 104 can be affixed at a distal end of the delivery wire 102, and the expansile funnel 106 can extend distally from the expansile tube 104. The clot retrieval device 100 including the delivery wire 102, expansile tube 104, and expansile funnel 106 can be sized to fit within the lumen 202 of the outer catheter 200. The device 100, 100a, 100b can, but need not include a defined transition between the expansile tube 104 and the expansile funnel 106.

During delivery of the system 10, 10a, 10b through vasculature, the device 100, 100a, 100b can be retained completely within the lumen 202 of the outer catheter 200 as the catheter 200 is translated through vasculature. Once the distal end of the catheter 200 is positioned near the obstruction (T), the delivery wire 102 can be pushed distally to move the expansile funnel 106 distally out of the lumen 202 of the catheter 200. The expansile funnel 106 can be expandable to circumferentially appose the walls of the blood vessel on the proximal side of the obstruction (T) while the expansile tube 104 remains positioned within the lumen 202 of the catheter 200. The distal mouth 108 of the expansile funnel 106 can have a circumference 210 when expanded in the blood vessel (BV) that is approximately equal to the circumference 212 of the interior of the blood vessel (BV). The expansile funnel 106 can therefore be expandable to an expanded deployed state having an outer circumference 210 that is greater than the circumference 208 of the lumen 202 of the outer catheter 200. The expansile funnel 106 can provide fluidic passage to a lumen 105 of the expansile tube 104. The lumen 105 of the expansile tube 104 can be in fluidic communication with the lumen 202 of the catheter 200 such that when the aspiration source (AS) is applied, the aspiration force can sufficiently reach the obstruction (T). The expansile tube 104 can expand to have an outer circumference that is approximately equal to the circumference 208 of the lumen 202 of the outer catheter 200.

The expansile tube 104 can be disposed proximate to the distal end of the delivery wire 102. The expansile tube 104 can be affixed to a plurality of connecting struts 120 disposed on the distal end of the delivery wire 102. The expansile tube 104 can expand and retract to accommodate delivery catheters having different diameters.

Referring collectively to FIGS. 1A, 1B, 2, and 3, the delivery wire 102 can be coated with hydrophilic and/or hydrophobic lubricious polymer including polyvinylpyrrolidone, polytetrafluoroethylene, or silicone to reduce friction between the components of the system 10, 10a, 10b and the components of the system 10, 10a, 10b and the blood vessel (BV). The delivery wire 102 can have sufficient flexibility for a physician to maneuver the clot retrieval device 100, 100a, 100b through the blood vessel (BV), but also sufficient stiffness to effectively guide the clot retrieval device 100, 100a, 100b to the target site. In one example, the delivery wire 102 can be solid steel. In another example, the delivery wire 102 can be a nitinol core wire. In one example, the distal end 103 of the delivery wire 102 can include a plurality of connecting struts 120. The connecting struts 120 can comprise the same material as the delivery wire 102. The connecting struts 120 can connect the distal end 103 of the delivery wire 102 to the expansile tube 104, as illustrated in FIG. 1B.

The expansile funnel 106 can be affixed to the distal end of the expansile tube 104. The expansile funnel 106 can be expanded from a collapsed delivery state to an expanded deployed state. In the collapsed delivery state, the expansile funnel 106 is sized to traverse the lumen 202 of the outer catheter 200. In this configuration, the expansile funnel 106 can be folded or collapsed upon itself in order to adequately fit within the lumen 202 of the outer catheter 200. The expansile funnel 106 can fold or collapse radially inward towards a longitudinal axis. In the collapsed delivery state, at least a portion of the expansile funnel 106 and the expansile tube 104 can have a common circumference. In the collapsed delivery state, the lumen 111 of a fluid-impermeable flexible tube 110, the lumen 105 of the expansile tube 104, and the lumen 202 of the outer catheter 200 can be aligned coaxially about a longitudinal axis (LA). In this configuration, the clot retrieval device 100 can be transported through the body using catheters of varying diameters until the clot retrieval device 100 is proximate to the obstruction (T) in the blood vessel (BV).

The expansile funnel 106 can assume the expanded configuration by self-extending radially outward from the longitudinal axis upon exiting the distal end of the outer catheter 200. In one example in which the expansile funnel 106 can be folded or compressed, when the expansile funnel 106 is in the collapsed delivery state, the expansile funnel 106 can provide a spring-like force that facilitates self-expansion of the expansile funnel 106 when the expansile funnel 106 exits the outer catheter 200. In the expanded deployed state, the expansile funnel 106 can expand such that the expansile funnel 106 has an outer circumference 210 greater than the circumference 208 of the lumen 202 of the outer catheter 200. In one example, the expansile funnel 106, when in the expanded deployed state, can have a circumference 210 approximately equal to the circumference 212 of the interior of the blood vessel (BV). The expansile funnel 106 can thus seal with the blood vessel (BV) or create enough of a restriction such that when aspiration is applied, blood and the clot distal of the distal mouth 108 of the expansile funnel 106 will be drawn into the clot retrieval device 100, 100a, 100b rather than blood proximal of the expansile funnel 106. In the expanded deployed state, at least a portion of the clot retrieval device 100 can be positioned within the lumen 202 of the outer catheter 200. In one example, in the expanded deployed state, approximately half of the clot retrieval device 100, 100a, 100b can be positioned within the lumen 202 of the outer catheter 200. The clot retrieval device 100, 100a, 100b can be positioned coaxially along a longitudinal axis (LA) within the lumen 202 of the outer catheter 202. In the expanded deployed state, at least a portion of the clot retrieval device 100, 100a, 100b can be positioned within the lumen of the blood vessel (BV). In one example, in the expanded deployed state, approximately half of the clot retrieval device 100, 100a, 100b can be positioned within the lumen of the blood vessel (BV).

The expansile funnel 106 can include a distal mouth 108. In the expanded deployed state, the distal mouth 108 can be open and configured to engage the obstruction (T). The open distal mouth 108 can have a circumference approximately equal to the circumference 212 of the blood vessel (BV). The distal mouth 108 can have a circumference approximately equal to or larger than the circumference of the obstruction (T). Because the open distal mouth 108 has a circumference approximately equal to or larger than the circumference of the obstruction, the distal mouth 108 of the expansile funnel 106 can engage and receive the obstruction (T). When the aspiration source is connected and suction begins, the obstruction expansile funnel 106 can further receive the obstruction (T), such that the obstruction (T) can be pulled into the expansile funnel 106, and particularly into the lumen 111 of the fluid-impermeable flexible tube 110. The expansile funnel 106 can be progressively compressed during retrieval of the obstruction (T) to a small diameter so that it can be fully received within the expansile tube 104 of the clot retrieval device 100, 100a, 100b. The obstruction (T) can then be safely and effectively removed from the patient. If the obstruction (T) does become lodged in the distal mouth 108, the open mouth 108 will protect the obstruction (T) and prevent it from dislodging as the aspiration suction is maintained and the clot retrieval device 100, 100a, 100b is retracted into the sheath or outer catheter 200.

The large distal mouth 108 of the clot retrieval device 100, 100a, 100b of systems 10, 10a, 10b illustrated herein can offer improved performance over conventional fixed-mouth designs. Traditional fixed-mouth catheters can be hindered by having firm, fibrin-rich clots lodge in the tip of a catheter, or by having softer portions of the clot shear away. When aspirating through a fixed-mouth catheter, a significant portion of the suction can be directed to fluid proximal of the tip, reducing the suction directed to the clot and the success rate of clot removal. As the diameter of an expandable distal mouth 108 can be close to that of the vessel, clot shearing at the mouth of the catheter can be mitigated and the volume of fluid and clot distal of the mouth secured. However, the expansile funnel 106 of the disclosed technology can increase the amount of suction force by increasing the cross-sectional area of engagement between the expansile funnel and the obstruction, resulting in more effective removal of an obstruction (T).

FIG. 1B is a cross-sectional view of the interior of the expansile tube 104 when the clot retrieval device 100 is in an expanded deployed state. As illustrated in FIG. 1B, the delivery wire 102 can include connecting struts 120. The connecting struts 120 can be fixed to the walls of the expansile tube 104. A fluid-impermeable flexible tube, membrane, coating, or other cover 110 can cover at least a portion of the outer walls of expansile tube 104. A seal 118 can form against the inner walls of the outer catheter 200 when the outer walls of the expansile tube 104 exert force on the inner walls of the outer catheter 200. The seal 118 can direct the aspiration source to the obstruction (T) and ensure the clot retrieval device 100 can capture the obstruction (T). The cover 110 can be affixed or integrated with the expansile tube 104 and otherwise configured to expand to create a seal between the outer surface of the membrane 110 and the inner walls of the lumen 202 of the outer catheter 200. The lumen 105 of the expansile tube 104 can be in fluid communication with the lumen 202 of the catheter 200 such that when the aspiration source (AS) is applied, the aspiration force can sufficiently reach the obstruction (T) with minimal to no flow between the membrane or cover 110 and the inner walls of the lumen 202.

The clot capture devices 100a, 100b illustrated in FIG. 2 and FIG. 3 can similarly include a cover 110 over the proximal portion 104 of the device 100a, 100b. The outer flexible tube 110a illustrated in FIG. 2 can extend to cover the proximal portion of the device 100a to form the cover 110 illustrated in FIG. 1B. The fluid-impermeable flexible tube 110a of the device 100a illustrated in FIG. 2 can include a lumen 111. The lumen 105 of the proximal expansile tube 104 can be in fluid communication with the lumen 111 of the fluid-impermeable flexible tube 110a, such that when the aspiration source (AS) is applied, the aspiration force can sufficiently reach the obstruction (T). Alternatively, the proximal expansile tube 104 of the device 100a illustrated in FIG. 2 can include a separate cover, coating, membrane, or seal to guide aspiration through the funnel 106 and catheter lumen 202.

Likewise, the cover 110b (fluid-impermeable flexible tube, membrane, coating, or other cover) of the device 100b illustrated in FIG. 3 can extend over the funnel 104 and tube 104 portions of the device 100b, or the funnel 106 and tube 104 can be non-uniformly covered. The cover 110b can extend within the expansile tube 104. The cover 110b can cover at least a portion of the inner walls of the expansile tube 104.

Referring collectively to FIGS. 1A, 1B, 2, and 3 the device 100, 100a, 100b can include a distal end 122. The distal end 122 can correspond to a distal end of the cover 110, 110a, 110b of the funnel 106 of the device 100, 100a, 100b. In examples where the cover 110, 110a, 110b extends to the proximal expansile tube 104 of the device 100, 100a, 100b, the distal end 122 of the cover 110, 110a, 110b can have a greater circumference 210 than a proximal end of the cover 110, 110a, 110b when the clot retrieval device 100, 100a, 100b is in the expanded deployed state. The distal end 122 can have a circumference at least the size of the circumference of the obstruction (T), allowing expansile funnel 106 including the cover 110, 110a, 110b to receive the obstruction (T) when an aspiration source (AS) is applied. The cover 110, 110a, 110b can include flexible, polymer material. For example, the cover 110, 110a, 110b can be formed from a ductile elastomer, which has the advantages of being soft and flexible with resistance to tearing and perforation due to a high failure strain. In one example, the cover 110, 110a, 110b can comprise urethane or other similar material. The cover 110, 110a, 110b can provide the clot retrieval device 100, 100a, 100b with advantageous properties, such as high tensile strength, resistance to degradation, biocompatibility, and flexibility. The fluid-impermeable flexible tube 110 can also be configured to minimize friction between the cover 110, 110a, 110b and the blood vessel (BV), reducing strain on the blood vessel (BV). The flexible nature of the cover 110, 110a, 110b can allow the cover 110, 110a, 110b to stretch as the expansile funnel 106 expands from the collapsed delivery state to the expanded deployed state. As the cover 110, 110a, 110b stretches, the cover 110, 110a, 110b can follow the contours of an underlying strut framework 116. In some examples, such as illustrated in FIG. 2, the cover 110a can include a flexible tube that can structurally support the strut framework 116a to maintain position of first and second rings 112, 114 of struts relative to each other. The cover 110a can further include a construction with sufficient structural integrity so that the strut framework 116a can be stitched to the cover 110a. The funnel 106 portion of the device 100a can therefore further include sutures or other stitching to affix the cover 110a to the framework 116a as illustrated in FIG. 2.

The strut framework 116a, 116b can have a variety of configurations that are not illustrated in FIG. 1A, 1B, 2, or 3. The configuration of the strut framework 116a, 116b can be such that the profile of the expansile funnel 106 in the expanded deployed state can hinge radially outward to have a portion appose the circumference 212 of the blood vessel (BV). The strut framework 116a, 116b can include a plurality of closed cells, loops, or undulations. In one example, the strut framework 116a, 116b can include a plurality of distal crowns. In one example, the strut framework 116a, 116b can have petal shaped cells with rounded edges. The petal shaped cells can open in the expanded deployed state to assume a maximum radial size.

In one example, the cover 110, 110a, 110b can include a fluid-impermeable flexible tube that provides the sole structural support of the expansile funnel 106. As illustrated in FIG. 2, the fluid-impermeable flexible tube 110a can provide the sole structural support of the expansile funnel 106 in the area between the first ring of struts 112 and the second ring of struts 114. As illustrated in FIG. 3, the strut framework 116 can provide support for the expansile funnel 106.

The ideal diameter of the clot retrieval device 100, 100a, 100b depends on the location of the target obstruction and the diameter of the outer catheter 200 through which the clot retrieval device 100, 100a, 100b can be delivered. For retrieval of clots in the cerebral vascular bed, where vessel diameters commonly around 3 mm to 6 mm, an applicable system might have an outer catheter 200 with an inner diameter of about 0.070 inches (1.8 mm) and a clot retrieval device 100 with an inner diameter of about 0.062 inches (1.6 mm). Upon deployment from the outer catheter 200, the maximum diameter of the expansile funnel 106 could be a minimum of 3 mm (but in some instances about 5-6 mm), allowing it to seal against the walls of the blood vessel (BV) and providing an opening at the distal mouth as large as the blood vessel (BV) itself.

FIGS. 4-6 include illustrations of an alternative system 10c for retrieving an obstruction (T) in a blood vessel (BV). The system 10c can include a catheter 200 and a funneled stent retriever 300 that includes an expandable framework 304 for engaging an obstruction (T), the framework 304 having a fluid-impermeable membrane, cover, or tube affixed to a proximal portion thereof. The obstruction (T) can include an occlusive clot within a blood vessel (BV) of a patient. The obstruction can include debris or other foreign material or mass within a blood vessel (BV). The outer catheter 200 can include a lumen 202 sized, shaped, and otherwise configured to slidably receive the funneled stent retriever 300. The catheter 200 can otherwise be sized and configured as illustrated and disclosed elsewhere herein. FIG. 4 illustrates the system 10c expanded through an obstruction (T) in a blood vessel (BV). FIG. 5 illustrates the system 10c expanded as illustrated in FIG. 4 with struts of the expandable framework 304 illustrated. FIG. 6 illustrates the funneled stent retriever 300 expanded without being restricted by the catheter 200 or the blood vessel (BV).

Referring collectively to FIGS. 4-6, the funneled stent retriever 300 can be disposed within the lumen 202 of the outer catheter 202 during delivery of the device. The funneled stent retriever 300 can move along a longitudinal axis as the system 10c approaches and engages with an obstruction (T).

The funneled stent retriever 300 can include an elongate flexible member 102, referred to herein generically as "a delivery wire". The delivery wire 102 can facilitate positioning the stent retriever 300 proximate to the obstruction (T). The delivery wire 102 can be coated with hydrophilic and/or hydrophobic lubricious polymer including polyvinylpyrrolidone, polytetrafluoroethylene, or silicone to reduce friction between the components of the system 10c and the components of the system 10c and the blood vessel (BV). The delivery wire 102 can have sufficient flexibility for a physician to maneuver the stent retriever 300 through the blood vessel (BV), but also sufficient stiffness to effectively guide the stent retriever 300 to the target site. In one example, the delivery wire 102 can be solid steel. In another example, the delivery wire 102 can be a Nitinol core wire. In one example, a distal end 103 of the delivery wire 102 can include a plurality of connecting struts 120. The connecting struts 120 can include the same material as the delivery wire 102. The connecting struts 120 can connect the distal end 103 of the delivery wire 102 to the expansile tube 104, as illustrated in FIGS. 4-6. The delivery wire 102 and connecting struts can be configured as otherwise illustrated and described herein.

The stent retriever 300 can include an expandable framework 304 configured to engage and capture the obstruction (T). The framework 304 is illustrated having a structure similar to as disclosed in U.S. Pat. No. 9,445,829 which is hereby incorporated by reference as if set forth in its entirety herein. Alternatively, the expanded framework 304 can have a structure similar to other known frameworks of stent retriever devices or variations thereof as understood by a person of ordinary skill in the art according to the teachings of the present disclosure. As a non-exhaustive list of such frameworks of stent retriever devices, U.S. Pat. Nos. 10,292,723, 8,852,205, 9,301,769, 10,229,881, 10,420,570, 10,201,360, and 10,363,054 and U.S. Pat. Pub. Nos. 2017/0071614 are hereby incorporated by reference as if set forth in their entirety herein.

The expandable framework 304 can be made of material capable of self-expanding to an expanded configuration once released from the collapsed delivery state, such as a shape memory material. Additionally, or alternatively, the expandable framework 304 can be made of super elastic material. In one example, the superlattice alloy can be Nitinol or an alloy of similar properties. In one example, the super elastic alloy can include nickel and titanium. The expandable framework 304 can have a plurality of forms. The expandable framework 304 can be manufactured by laser cutting a Nitinol tube and then applying heat and electropolish to create a desired framework. The expandable framework 304 can include a radiopaque marker that can allow the expandable framework 304 to be visible using fluoroscopy.

When the expandable framework 304 is in an expanded deployed configuration, the expandable framework 304 can have a substantially tubular shape. In the expanded deployed configuration, the expandable framework 304 can include a tubular portion 310, a proximal portion 306 and a distal portion 312. The tubular portion 310 can extend distally from the proximal portion 306. The proximal portion 306 of the expandable framework 304 can be fixed to the distal end 103 of the delivery wire 102. In one example, the proximal portion 306 can be fixed to the distal end 103 of the delivery wire 102 by a collar joint 316, as illustrated in FIG. 6. The collar joint 316 can include features and functionality of one or more collar joints disclosed elsewhere, for example in U.S. patent application Ser. Nos. 16/150,024 and 16/667,454 each incorporated by reference as if set forth in their entirety herein.

In an alternate example, the proximal portion 306 can be welded to the distal end 103 of the delivery wire 102. When the expandable framework 304 is in an expanded deployed configuration, the proximal portion 306 of the expandable framework 304 can be tapered, such that the proximal portion 306 narrows from the tubular portion 310 to the point at which the expandable framework 304 can be fixed to the delivery wire 102. The tapering of the proximal portion 306 can create a funnel-like shape, as illustrated in FIGS. 4-6. The distal portion 312 can extend distally from the tubular portion 310. When the expandable framework 304 is in an expanded deployed configuration, the distal portion 312 can taper, such that the distal portion 312 narrows from the tubular portion to a distal junction 326. The distal portion 312 can be closed, having cell openings sized sufficiently small to inhibit clot material from traveling distally from the interior of the framework 304 through the distal portion 312. Alternatively, funnel stent retriever need not include a tapered or closed distal portion 312, for instance, the distal end of the framework 304 can be open.

The tapering of the distal portion 312 can create a conical or funnel-like shape, as illustrated in FIGS. 4-6. The distal portion 312 can include a distal coil 328, as illustrated in FIG. 6. The distal coil 328 and the distal portion 312 can attach at a distal junction 326. The distal junction 326 can be a collared joint.

The ideal diameter of the expandable framework can depend on the location of the target obstruction and the diameter of the outer catheter through which the expandable framework 304 is delivered. For retrieval of clots in the internal carotid artery, where vessel diameters can be between approximately 3 mm and 6 mm, an applicable system 10c can include an expandable framework 304 of between approximately 3 mm and 6 mm. In one example, the expandable framework 304 can be slightly greater than the diameter of the blood vessel (BV), forming a seal with the inner walls of the blood vessel. The ideal length of the expandable framework 304 can depend on the location of the target and characteristics of the obstruction (T). In one example, the length of the expandable framework 304 can be approximately 30 mm. In another example, the length of the expandable framework can be approximately 40 mm.

As illustrated in FIG. 6, in one example, the expandable framework 304 can include an inner body 318 and an outer body 320. The inner body 318 can be disposed within the outer body 320. The inner body 318 can have a substantially longitudinal, tubular shape and traverse the length of the tubular portion 310 of the expandable framework 304. The inner body 318 and the outer body 320 can be connected to distal end 103 of the delivery wire 102. The inner body 318 can include a distal portion 324 proximate to the distal portion 312 of the expandable framework 304. The distal portion 324 of the inner body 318 can have a particular wire configuration that can facilitate engagement with an obstruction (T) and prevent the fragments of the obstruction from escaping the expandable framework 304. The particular wire configuration can have a substantially vertically-oriented ellipse shape. The particular wire configuration can be affixed to the inner body 318, the outer body 320, or both.

The stent retriever 300 can include a fluid-impermeable membrane 308. The fluid-impermeable membrane 308 can be affixed to the proximal portion 306 of the expandable framework 304. The fluid-impermeable membrane 308 can also be affixed to the expandable framework 304 extending into the lumen 202 of the outer catheter 200. The fluid-impermeable membrane 308 can be made of porous material. The porous material can include pores sized to be smaller than the size of blood molecules, thereby preventing blood molecules from passing through the fluid-impermeable membrane 208. The flexible nature of the fluid-impermeable membrane 308 allows the fluid-impermeable membrane 308 to stretch as the expandable framework expands from the collapsed delivery state to the expanded deployed state. As the fluid-impermeable membrane 308 stretches, the membrane 308 can follow the contours of an underlying expandable framework 304. In one example, the fluid-impermeable membrane 308 can cover at least a portion of the proximal portion 306 of the expandable framework 304. In another example, the fluid-impermeable membrane 308 can cover the entire proximal portion 306 of the expandable framework. The fluid-impermeable membrane 308 can cover the proximal portion 306 of the expandable framework 304 extending into the lumen 202 of the outer catheter 200. When the fluid-impermeable membrane 308 covers at least a portion of the proximal portion 306 of the expandable framework 304 and the expandable framework 304 extending into the lumen 202 of the outer catheter 200, a funnel-like shape can be created. The fluid-impermeable membrane 308 can include a proximal opening sized to permit aspiration. In the expanded deployed configuration, the circumference of the proximal opening can be approximately equal to the circumference 208 of the lumen 202 of the outer catheter 200. When an aspiration force is applied, the proximal opening can permit aspiration through the funnel-like shape of the fluid-impermeable membrane, facilitating retrieval of the obstruction (T).

The expandable framework 304 can have a collapsed delivery configuration and an expanded deployed configuration. In the collapsed delivery configuration, system 10c can include a microcatheter 204. The microcatheter 204 can be sized to traverse the lumen 202 of the outer catheter 200. In the collapsed delivery configuration, the expandable framework 304 can collapse into itself such that the expandable framework 304 can be positioned within the lumen 205 of the microcatheter 204.

In the collapsed delivery state, the first outer circumference 212 and the second outer circumference 214 of the fluid-impermeable membrane 308 can be approximately equal. The first circumference 212 and the second circumference 214 can be approximately equal to the circumference 220 of the lumen 205 of the microcatheter 204. In the collapsed delivery state, the first circumference 212, the second outer circumference 214, the circumference 330 of the tubular portion 310 of the expandable framework 304, and the circumference 220 of the lumen 205 of the microcatheter 204 can be approximately equal.

In the expanded deployed state, the tubular portion 310 of the expandable framework 304 can expand such that the circumference 330 of the tubular portion 310 is substantially equal to the circumference 212 of the blood vessel (BV). In one example, the funneled stent retriever 300 can be configured to treat an obstruction (T) having a circumference that is substantially equal to the circumference of the blood vessel (BV). In another example, the funneled stent retriever 300 can be configured to treat an obstruction (T) having a circumference smaller than the circumference of the blood vessel (BV). Because the tubular portion 310 can expand such that its circumference can be substantially equal to the circumference of the blood vessel (BV), the expandable framework 304 can fully engage with the obstruction (T).

In the expanded deployed state, the fluid-impermeable membrane can include a first outer circumference 212 and a second outer circumference 214. The first outer circumference 212 can be approximately equal to the circumference 208 of the lumen 202 of the outer catheter 200, as illustrated in FIG. 5. The second outer circumference 214 can be approximately equal to an inner circumference 212 of a blood vessel (BV), as illustrated in FIG. 5. The difference in circumferences 212, 214 of the fluid-impermeable membrane 308, can allow the membrane 308 to have a substantially funnel shape in the expanded deployed configuration.

In the expanded deployed state, the portion of the proximal portion 306 of the expandable framework 304 extending into the lumen 202 of the outer catheter 200 can create an outward force on the inner walls of the outer catheter 200. The outward force can be sufficient to create a fluid-impermeable seal 332 between the fluid-impermeable membrane 308 covering the proximal portion of the expandable framework 304 extending into the lumen 202 of the outer catheter 200 and lumen 202 of the outer catheter 200, as illustrated in FIG. 5. The fluid-impermeable seal 332 can facilitate aspiration and thus, removal of the obstruction (T) from the blood vessel (BV), as the aspiration suction is directed to the obstruction (T).

FIGS. 7A-7D and 8A-8H illustrate methods of removing an obstruction (T) from a blood vessel (BV) using a system 10c including a stent retriever 300 with an expandable framework 304. FIGS. 7A-7D are drawings at the target site illustrating delivery of a stent retriever 300 to the target site and capture of the obstruction (T). FIGS. 8A-8H are drawings of vasculature near the target site illustrating delivery of the stent retriever 300 to the target site, capture of the obstruction (T), and removal of the stent retriever 300 from the patient's body. The drawings of FIGS. 8A-8H are based on photographs of a prototype system 10c retrieving a clot (T) in a silicone model of vasculature near the Circle of Willis.

FIGS. 9A and 9B illustrate significant improvements clot retrieval devices 100a, 100b, 300 can provide compared to other commercially available products. FIG. 9A illustrates data comparing dimensions and operation of a prototype clot retrieval device constructed similar to devices 100a, 100b illustrated in FIGS. 2 and 3. FIG. 9B illustrates data comparing dimensions and operation of a prototype clot retrieval device constructed similar to device 300 illustrated in FIGS. 4 through 8H.

Optimal retrieval of an obstruction (T) from a blood vessel (BV) can depend on obstruction removal force. Obstruction removal force can be defined as the product of vacuum pressure applied multiplied by the cross-section area of the clot retrieval device engaging the obstruction (T). When the thrombus removal force is high, the obstruction (T) can be firmly held to the clot retrieval device, resulting in effective removal of the obstruction (T). Increasing the vacuum pressure applied can be one method of increasing the obstruction removal force. However, vacuum pressure can only be increased to a realistic limit (e.g. based on design constraints as understood by a person of ordinary skill in the art). Further, increasing the internal diameter, and thus, cross-section area of a catheter can present challenges, as larger catheters can be more difficult to track and can increase the potential for vessel damage.

Accordingly, clot retrieval devices 100a, 100b, and 300 as disclosed herein are configured to significantly increase the cross-section area engaging the obstruction (T), and thus increase the obstruction removal force as compared to commercially available products. By way of example, as illustrated in FIGS. 9A and 9B, the expansile funnel 106 of clot retrieval device 100a, 100b and the funneled stent retriever 300 can each expand to a distal internal diameter of approximately equal to an internal diameter of a blood vessel in which the device 100a, 100b, 300 is deployed. Assuming a blood vessel having an internal diameter of 0.16 inches or approximately 4 millimeters, regardless of the specific embodiment of the device 100a, 100b, 300, the device can expand to have a distal internal diameter of approximately 4 millimeters and can have a cross-section area of approximately 0.030 square inches or $2.0\times(10^{-5})$ square meters. When approximately 29 Hg (98000 Pascals) of vacuum pressure is applied, the resulting obstruction removal force at the expansile funnel can be approximately 1.2 Newtons (approximately 127 gram-force), regardless of the specific embodiment of the device 100a, 100b, 300. In contrast, when commercially available catheters, as identified in FIG. 9A, having a distal internal diameter of approximately 0.070 inches or 1.8 millimeters and a cross-section area of approximately 0.003 square inches or $2.0\times(10^{-6})$ square meters are subjected to a vacuum pressure of approximately 98000 Pascals, the resulting obstruction removal force at the catheter tip can be from approximately 0.21 to approximately 0.26 Newtons (approximately 21 to 27 gram-force). In this instance, clot retrieval device 100a, 100b, 300 can provide a cross-section area at the tip of the clot retrieval device 100a, 100b, 300 of approximately 1,000% larger than other commercially available products resulting in an obstruction removal force approximately 500% higher than other commercially available products.

FIG. 10 graphically illustrates the significantly increased obstruction removal force clot retrieval device 100a, 100b, 300 can provide as compared to commercially available products. In the illustrated example, EMBOVAC has the highest thrombus holding force of approximately 26 gram-force and the highest tip cross sectional area of $2.6\times(10^{-6})$ square meters of the tested commercially available devices. Clot retrieval devices 100a, 100b, 300 of the present disclosure have a tip cross sectional area and holding force of more than 4 times (nearly 5 times) that of the EMBOVAC. Further, the cross sectional area (and therefore holding force) of the clot retrieval devices 100a, 100b, 300 are limited in this illustration by the 4 millimeter vessel diameter, therefore the tip cross sectional area and holding force can be greater in a blood vessel having a larger diameter.

Figure 11:
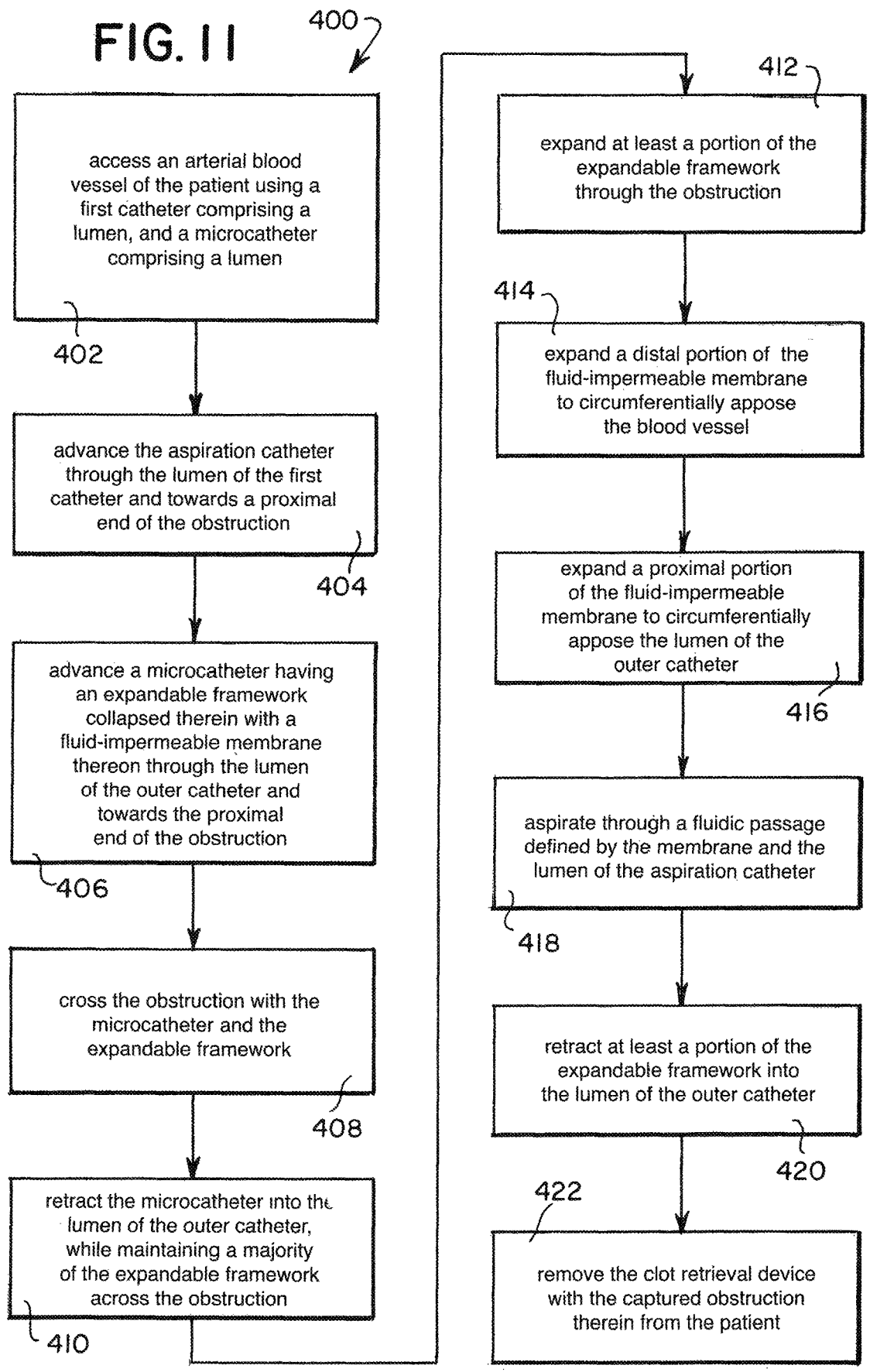
FIG. 11 is a flow diagram outlining steps for removing an obstruction from a blood vessel according to aspects of the present invention.

FIG. 11 is a flow diagram illustrating the method 400 of delivering a system including a funneled stent retriever 300 to a target site, capturing an obstruction, and removing the stent retriever 300 from the patient's body. The method can include one or more of the following steps presented in no particular order. The example method 400 can include additional steps as appreciated and understood by a person of ordinary skill in the art. The example method can be performed by an example device as disclosed herein, a variation thereof, or an alternative thereto as appreciated and understood by a person of ordinary skill in the art.

An artery of the brain can be accessed using a long guide wire 216. Once a distal tip of the guide wire 216 reaches the target site, the guide wire 216 can act as a guide that larger catheters can follow for delivery to the target site. The guide wire 216 can be constructed from solid steel, nitinol core, or other suitable material. In one example, vasculature can be accessed using a guide catheter such as a balloon catheter.

In step 402, an arterial blood vessel of a patient can be accessed using a first catheter 206 comprising a lumen 207, an aspiration catheter 200 comprising a lumen 202, and a microcatheter 204 comprising a lumen 205. As illustrated in FIGS. 7A and 8A, the first catheter 206 can have the largest diameter of the catheter delivery system. The first catheter 206 can be the initial catheter that enters the blood vessel (BV) of the patient. The aspiration catheter 200 can be disposed within the lumen 207 of the first catheter 206. The aspiration catheter 200 can be the second catheter that enters the blood vessel (BV) of the patient. The microcatheter 204 can be disposed within the lumen 202 of the aspiration catheter 200. The microcatheter can have the smallest diameter of the delivery catheter system and can be sized to receive the stent retriever 300 within its lumen 205. The catheters 206, 200, 204 can be advanced over a guide wire 216 positioned across the obstruction (T) as illustrated in FIGS. 7A and 8A.

In step 404, the aspiration catheter 200 can be advanced through the lumen 207 of the first catheter 206 and towards a proximal end of the obstruction (T) using conventionally known techniques, as illustrated in FIGS. 7A and 8B. In one example, the outer catheter 200 is advanced through the lumen 207 of the first catheter 206 until the outer catheter 200 is approximately three millimeters away from the obstruction (T).

In step 406, a microcatheter 204 having an expandable framework 304 collapsed therein can be advanced through the lumen 202 of the outer catheter 200 and towards the proximal end of the obstruction (T) as illustrated in FIGS. 7A and 8A. The expandable framework 304 can include a fluid-impermeable membrane 308 affixed thereto that is collapsed within the lumen 207 of the microcatheter 204 as the microcatheter 204 is advanced. The guide wire 216 and the outer catheter 200 can be manipulated as necessary while advancing the microcatheter 204 towards the obstruction (T).

In step 408, the microcatheter 204 having the expandable framework 304 collapsed within the lumen 207 of the microcatheter 204 can cross the obstruction (T), as illustrated in FIGS. 7B and 8C. The guide wire 216 can subsequently be removed from the system 10c. The expandable framework 304 can be advanced through the microcatheter 204 until the distal end of the expandable framework 304 breaches the distal tip of the microcatheter 204 as illustrated in FIG. 8D.

In step 410, the microcatheter 204 can be retracted into the lumen 202 of the outer catheter 200, while a majority of the expandable framework 304 remains across the obstruction (T), as illustrated in FIGS. 7C, 7D, 8E, and 8F.

In step 412, at least a portion of the expandable framework 304 can be expanded to engage the obstruction (T), as illustrated in FIGS. 7C, 7D, 8E, and 8F. As the microcatheter 204 is retracted into the lumen 202 of the outer catheter 200 in step 410, the expandable framework 304 can self-expand. Additionally, or alternatively, the expandable framework 304 can exhibit a spring force while the expandable framework 304 is within the lumen 205 of the microcatheter 204 that acts to facilitate a spring-like expansion when the expandable framework 304 is moved out of the lumen 205 of the microcatheter 204.

Figure 8F:
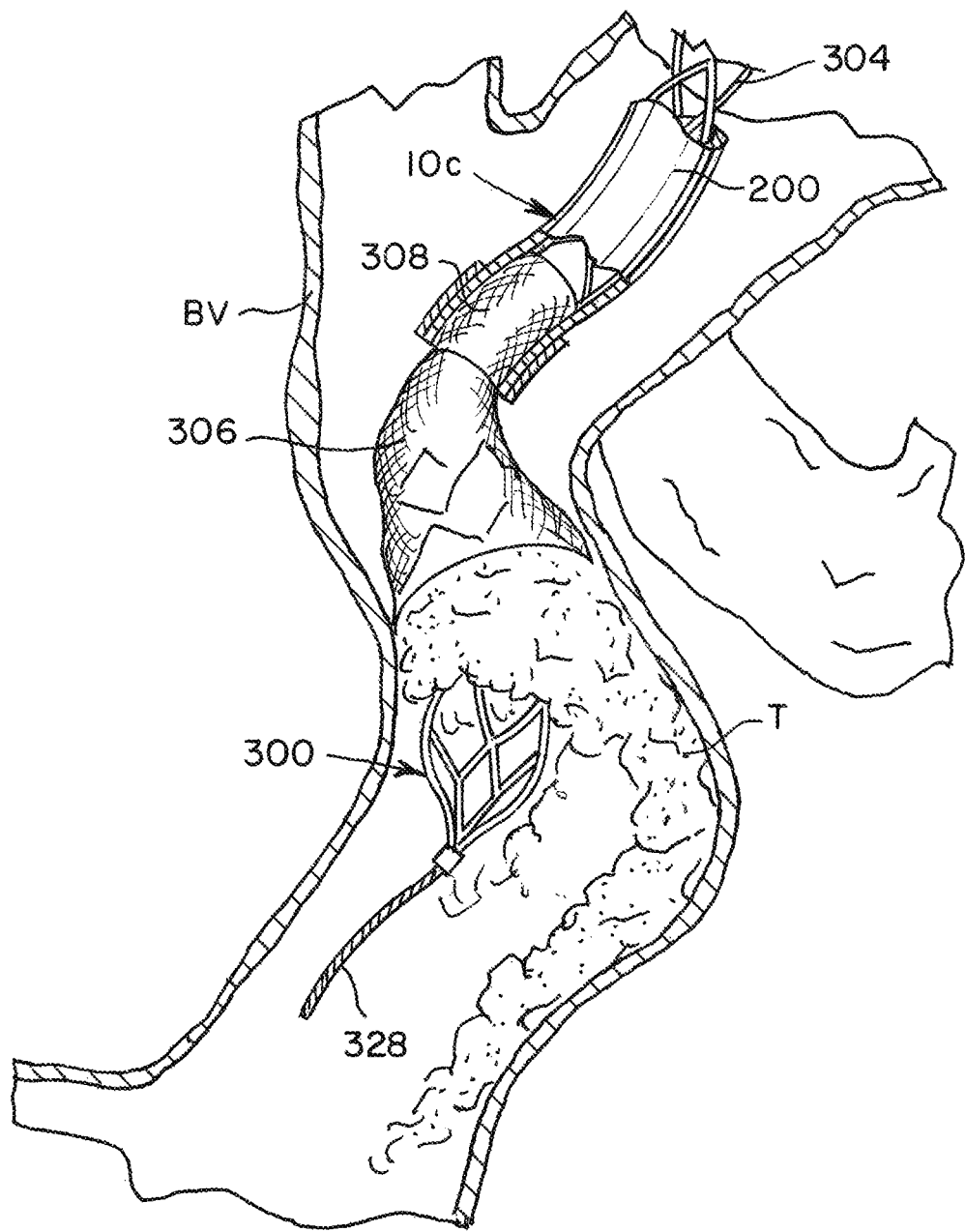

In step 414, a distal portion of the fluid-impermeable membrane 308 can be expanded, as illustrated in FIGS. 8E and 8F. In one example, the distal portion of the fluid-impermeable membrane 308 can be expanded to circumferentially appose the blood vessel (BV). In this configuration, the fluid-impermeable membrane 308 is proximate to the inner walls of the blood vessel (BV).

Figure 7D:
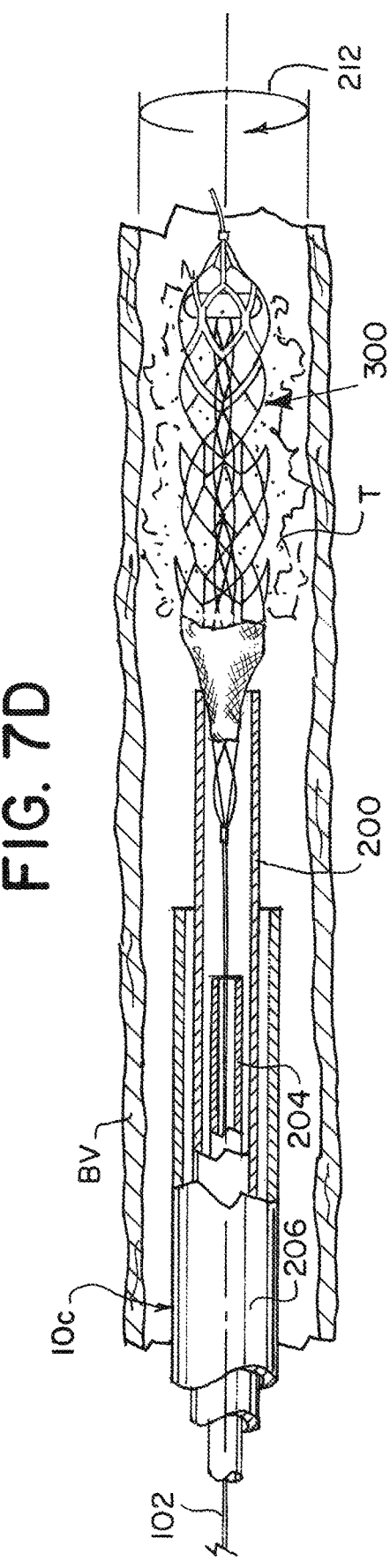

In step 416, a proximal portion of fluid-impermeable membrane 308 can be expanded, as illustrated in FIGS. 7D, 8E, and 8F. In one example, the proximal portion of the fluid-impermeable membrane 308 can be expanded to circumferentially appose the lumen 202 of the outer catheter 200. In this configuration, the fluid-impermeable membrane 308 can form a seal 332 against the inner walls of the outer catheter 200.

In step 418, an aspiration source can be connected to the system 10c. The aspiration source can generate a vacuum pressure that can aspirate through a fluidic passage defined by the fluid-impermeable membrane 308 and the lumen 202 of the aspiration catheter 200. The suction can be sufficient to engage the stent retriever 300 and the obstruction (T) during removal of the obstruction.

In step 420, at least a portion of the expandable framework 304 can be retracted into the lumen 202 of the outer catheter 200, as illustrated in FIG. 8G. The expandable framework 304 can be retracted into the lumen 202 of the outer catheter 200 until a physician can feel a significant tactile force. The significant tactile force can signify the obstruction (T) is successfully positioned within the distal end of the outer catheter 200. At this time, the aspiration source can be substantially restricted or eliminated.

Figure 8H:
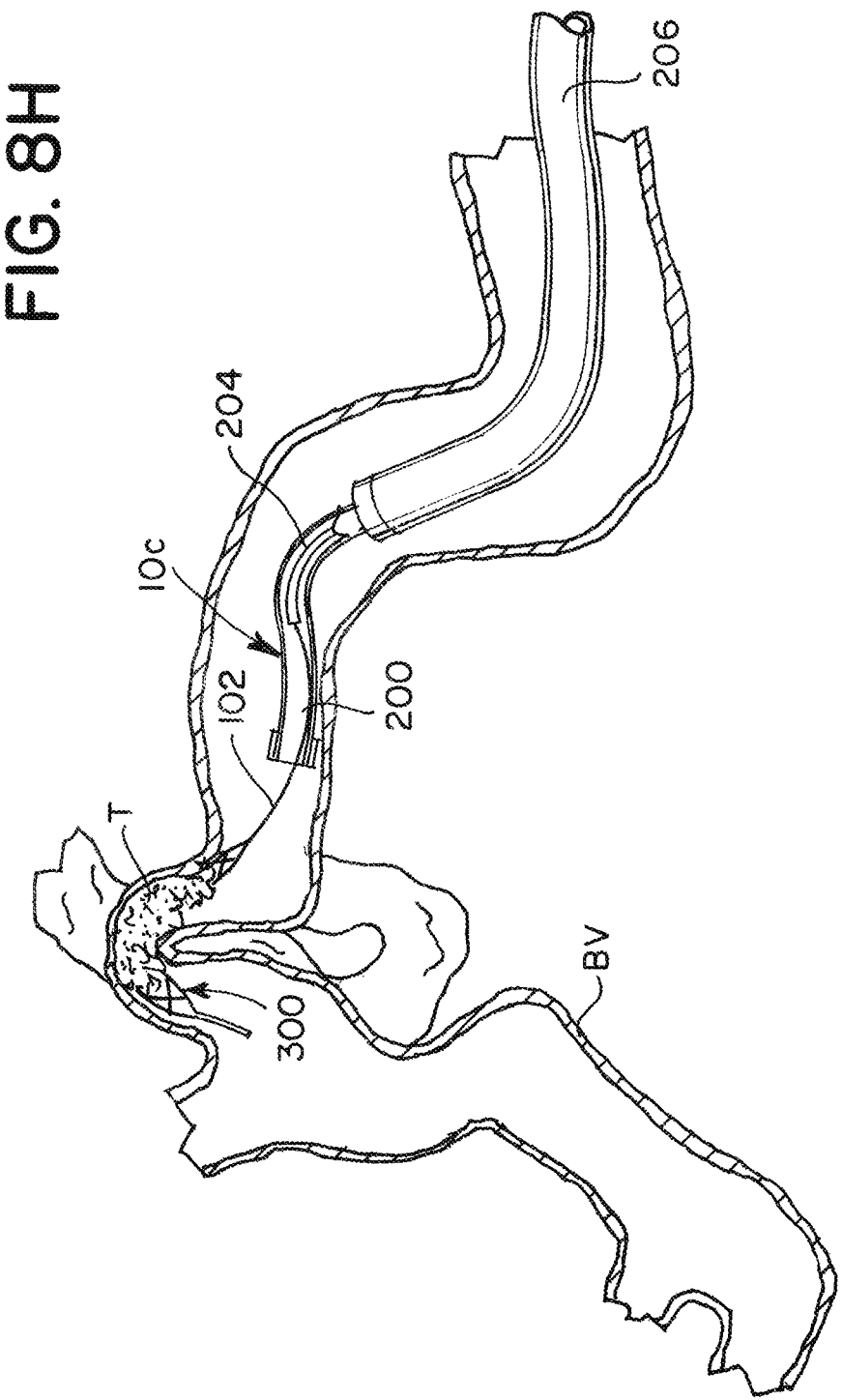

In step 422, the stent retriever 300 can be removed with the captured obstruction (T) from the patient as illustrated in FIG. 8H.

In one example, the contrast media can be injected within the lumen 202 of the outer catheter 200 to access the degree of obstruction remaining in the blood vessel (BV). The contrast media can include an iodine-based contrast material The invention is not limited to the examples described, which can be varied in construction and detail. The terms "distal" and "proximal" are used throughout the preceding description and are meant to refer to a positions and directions relative to a treating physician. As such, "distal" or "distally" refer to a position distant to or a direction away from the physician. Similarly, "proximal" or "proximally" refer to a position near to or a direction towards the physician.

In describing example embodiments, terminology is resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method can be performed in a different order than those described herein without departing from the scope of the disclosed technology. Similarly, it is also to be understood that the mention of one or more components in a device or system does not preclude the presence of additional components or intervening components between those components expressly identified.

As discussed herein, a "patient" or "subject" can be a human or any animal. It should be appreciated that an animal can be a variety of any applicable type, including, but not limited to, mammal, veterinarian animal, livestock animal or pet-type animal, etc. As an example, the animal can be a laboratory animal specifically selected to have certain characteristics similar to a human (e.g., rat, dog, pig, monkey, or the like).

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 99%.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

It must also be noted that, as used in the specification and the appended claims, the singular forms "a," "an," and "the" include plural referents unless the context clearly dictates otherwise. Ranges can be expressed herein as from "about" or "approximately" one particular value and/or to "about" or "approximately" another particular value. When such a range is expressed, other exemplary embodiments include from the one particular value and/or to the other particular value.

The descriptions contained herein are examples of embodiments of the invention and are not intended in any way to limit the scope of the invention. While particular examples of the present invention are described, various modifications to devices and methods can be made without departing from the scope and spirit of the invention. For example, while the examples described herein refer to particular components, the invention includes other examples utilizing various combinations of components to achieve a described functionality, utilizing alternative materials to achieve a described functionality, combining components from the various examples, combining components from the various example with known components, etc. The invention contemplates substitutions of component parts illustrated herein with other well-known and commercially-available products. Modifications recognized by one having ordinary skill in the art to which this invention relates are intended to be within the scope of the claims which follow.

What is claimed is:

1. A system for retrieving an obstruction in a blood vessel, the system comprising:
   an outer catheter comprising a lumen therethrough; and
   a clot retrieval device disposed within the outer catheter and translatable through the lumen of the outer catheter, the clot retrieval device comprising:
   an elongate flexible member comprising a distal end;
   an expandable framework, configured to engage the obstruction, expandable from a collapsed delivery configuration to an expanded configuration, the expandable framework comprising a proximal portion affixed to the distal end of the elongate flexible member and a tubular portion extending distally from the proximal portion, the tubular portion comprising an elongated tubular shape when the expandable framework is in the expanded configuration, and the proximal portion tapering proximally from the tubular portion to the distal end of the flexible member when the expandable framework is in the expanded configuration; and
   a fluid-impermeable membrane affixed to the proximal portion of the expandable framework when the expandable framework is in the expanded configuration, the fluid-impermeable membrane further affixed to the tubular portion and extending into the lumen of the outer catheter when the expandable framework is in the expanded configuration, the fluid-impermeable membrane terminating distal of a proximal end of the expandable framework, and the fluid-impermeable membrane comprising a funnel shape around the proximal portion of the expandable framework when the expandable framework is in the expanded configuration,
   wherein a majority of the tubular portion of the expandable framework comprises cell openings sized to pass through the obstruction when the expandable framework expands from the collapsed delivery configuration to the expanded configuration.

2. The system of claim 1, wherein the expandable framework further comprises a closed distal end portion extending distally from the tubular portion and radially inward to a central axis of the tubular portion.

3. The system of claim 1, further comprising:
   a microcatheter sized to traverse the lumen of the outer catheter,
   wherein the expandable framework is sized to traverse a lumen of the microcatheter when the expandable framework is in the collapsed delivery configuration.

4. The system of claim 1, wherein the tubular portion is expandable to circumferentially appose a lumen of the blood vessel when the expandable framework is in the expanded configuration.

5. The system of claim 1, wherein, when the expandable framework is in the expanded configuration, the fluid-impermeable membrane comprises a first outer circumference approximately equal to an inner circumference of the lumen of the outer catheter, and a second outer circumference approximately equal to an inner circumference of the blood vessel.

6. The system of claim 1,
   wherein when the expandable framework is in the expanded configuration, at least a portion of the proximal portion of the expandable framework is positioned within the lumen of the outer catheter, providing an outward force to the lumen of the outer catheter, and
   wherein the force is effective to create a fluid-impermeable seal between the fluid-impermeable membrane and the lumen of the outer catheter.

7. A system for retrieving an obstruction in a blood vessel, the system comprising:
   an outer catheter comprising a lumen therethrough; and
   a clot retrieval device disposed within the outer catheter and translatable through the lumen of the outer catheter, the clot retrieval device comprising:
   an elongate flexible member comprising a distal end;
   an expandable framework, configured to engage the obstruction, expandable from a collapsed delivery configuration to an expanded configuration, the expandable framework comprising a proximal portion affixed to the distal end of the elongate flexible member and a tubular portion extending distally from the proximal portion, the tubular portion comprising an elongated tubular shape when the expandable framework is in the expanded configuration, and the proximal portion tapering proximally from the tubular portion to the distal end of the flexible member when the expandable framework is in the expanded configuration; and
   a fluid-impermeable membrane affixed to the proximal portion of the expandable framework when the expandable framework is in the expanded configuration, the fluid-impermeable membrane further affixed to the tubular portion and extending into the lumen of the outer catheter when the expandable framework is in the expanded configuration, the fluid-impermeable membrane terminating distal of a proximal end of the expandable framework, and the fluid-impermeable membrane comprising a funnel shape around the proximal portion of the expandable framework when the expandable framework is in the expanded configuration, wherein the expandable framework further comprises a closed distal end portion extending distally from the tubular portion and radially inward to a central axis of the tubular portion.

8. The system of claim 7, further comprising:

a microcatheter sized to traverse the lumen of the outer catheter, wherein the expandable framework is sized to traverse a lumen of the microcatheter when the expandable framework is in the collapsed delivery configuration.

9. The system of claim 7, wherein the tubular portion is expandable to circumferentially appose a lumen of the blood vessel when the expandable framework is in the expanded configuration.

10. The system of claim 7, wherein, when the expandable framework is in the expanded configuration, the fluid-impermeable membrane comprises a first outer circumference approximately equal to an inner circumference of the lumen of the outer catheter, and a second outer circumference approximately equal to an inner circumference of the blood vessel.

11. The system of claim 7, wherein when the expandable framework is in the expanded configuration, at least a portion of the proximal portion of the expandable framework is positioned within the lumen of the outer catheter, providing an outward force to the lumen of the outer catheter, and wherein the force is effective to create a fluid-impermeable seal between the fluid-impermeable membrane and the lumen of the outer catheter.

* * * * *